United States Patent
Glimcher et al.

(10) Patent No.: US 6,410,261 B2
(45) Date of Patent: *Jun. 25, 2002

(54) CIITA-INTERACTING PROTEINS AND METHODS OF USE THEREFOR

(75) Inventors: Laurie H. Glimcher, West Newton, MA (US); Hong Zhou, Wilmington, DE (US)

(73) Assignee: President and Fellows of Harvard College, Cambridge, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/965,272

(22) Filed: Nov. 6, 1997

(51) Int. Cl.[7] .......................... C07H 21/02; C12N 15/00; C12P 21/06; C07K 1/00
(52) U.S. Cl. ................... 435/69.1; 536/23.1; 536/23.5; 435/320.1; 435/325; 435/455; 435/252.3; 530/350
(58) Field of Search ............................... 536/23.1, 23.5; 435/320.1, 325, 252.3, 69.1, 455; 530/350

(56) References Cited

FOREIGN PATENT DOCUMENTS

| EP | 0 638 836 A1 | 4/1995 |
|---|---|---|
| WO | 96/06107 | 2/1996 |

OTHER PUBLICATIONS

Nagase et al DNA Res. 4(2):141–150, 1997.*
Geneseq Acc. No. AB002344 Accessed by US–PTO on Feb. 3, 2000*
Ngo, in The Protein Folding Problem and Tertiary Structure Prediction, Merz et al. (eds.), Birkhauser Boston: Boston, MA, pp. 433 and 492–495, 1994.*
Rudinger (in Peptide Hormones, Parsons (ed.), University Park Press: Baltimore, MD, pp. 1–7, 1976.*
Bontron, S. et al., "Two novel mutations in the MHC class II transactivator CIITA in a second patient from MHC class II deficiency complementation group A" *Hum. Genet.* 99:541–546 (1997).
Chang, C–H. et al., "Mice Lacking the MHC Class II Transactivator (CIITA) Show Tissue–Specific Impairment of MHC Class II Expression" *Immunity* 4:167–178 (1996).
Greenfield et al., GenBank Accession No. Y09222 (Feb. 1997).
Hillier et al., GenBank Accession No. AA158658 (Mar. 1998).
Hillier et al., GenBank Accession No. AA159068 (Mar. 1998).
Mach, B. et al., "Regulation of MHC Class II Genes: Lessons from a Disease" *Annu. Rev. Immunol.* 14:301–331 (1996).

Marra et al., GenBank Accession No. AA123018 (Feb. 1997).
Marra et al., GenBank Accession No. AA153422 (Feb. 1997).
Marra et al., GenBank Accession No. AA153713 (Feb. 1997).
Marra et al., GenBank Accession No. AA165993 (Feb. 1997).
Marra et al., GenBank Accession No. W44115 (May 1996).
Marra et al., GenBank Accession No. W81758 (Sep. 1996).
Mazeyrat et al., GenBank Accession No. 3786392 (Oct. 1998).
Nagase et al., GenBank Accession No. 2280480 (Jul. 1997).
Nagase et al., GenBank Accession No. AB002344 (Jul. 1997).
Nagase, T. et al., "Prediction of the Coding Sequences of Unidentified Human Genes. VII. The Complete Sequences of 100 new cDNA Clones from Brain Which Can Code for Large Proteins in vitro" *DNA Research* 4:141–150 (1997).
Riley, J.L. et al. "Activation of Class II MHC Genes Requires Both the X Box Region and the Class II Transactivator (CIITA)" *Immunity* 2:533–543 (1995).
Steimle, V. et al., "Complementation Cloning of an MHC Class II Transactivator Mutated in Hereditary MHC Class II Deficiency (or Bare Lymphocyte Syndrome)" *Cell* 75:135–146 (1993).
Steimle, V. et al., "Major Histocompatibility Complex Class II Defieciency: A Disease of Gene Regulation" in Advances in Immunology, vol. 61, Academic Press, Inc., pp. 327–340 (1996).
Steimle, V. et al., "Regulation of HMC Class II Expression by Interferon –γMediated by the Transactivator Gene CIITA" *Science* 265:106–109 (1994).
Wilson et al., GenBank Accession No. U23513 (Nov. 1996).
Zhou, H. and Laurie H. Glimcher, "Human MHC Class II Gene Transcription Directed by the Carboxyl Terminus of CIITA, One of the Defective Genes in Type II MHC Combined Immune Deficiency" *Immunity* 2:545–553 (1995).

(List continued on next page.)

*Primary Examiner*—Scott D. Priebe
(74) *Attorney, Agent, or Firm*—Lahive & Cockfield, LLP; Giulio A. DeConti, Jr., Esq.; Cynthia L. Kanik

(57) ABSTRACT

Isolated nucleic acid molecules encoding a novel protein, CIP104, that interacts with CIITA, an MHC class II transcriptional activator, are disclosed. The invention further provides antisense nucleic acid molecules, recombinant expression vectors containing a nucleic acid molecule of the invention, host cells into which the expression vectors have been introduced and non-human transgenic animals carrying a CIP104 transgene. The invention further provides isolated CIP104 proteins and peptides, CIP104 fusion proteins and anti-CIP104 antibodies. Methods of using the CIP104 compositions of the invention are also disclosed, including methods for detecting CIP104 activity (e.g., CIP104 protein or mRNA) in a biological sample, methods of modulating CIP104 activity in a cell, and methods for identifying agents that modulate an interaction between CIP104 and CIITA.

8 Claims, 4 Drawing Sheets

OTHER PUBLICATIONS

Chin, Keh–Chuang et al, (1997) "Activation and Transdominant Suppression of MHC Class II and HLA–DMB Promoters By A Series of C–Terminal Class II Transactivator Deletion Mutants", The Journal of Immunology, pp. 2789–2794.

Nagase, T. et al. (1997) "Prediction Of The Coding Sequences Of Unidentified Human Genes VII. The Complete Sequences of 100 New cDNA Clones From Brain Which Can Code For Large Proteins In Vitro", EMBL Sequences DataBase.

Zhou, Hong et al. (1997) "CIITA–Dependnet and Independent Class II MHC Expression Revealed By A Dominant Negative Mutant", The Journal of Immunology, vol. 158 pp. 4741–4749.

* cited by examiner

CIITA-INTERACTING PROTEINS AND METHODS OF USE THEREFOR

GOVERNMENT FUNDING

Work described herein was supported, at least in part, under grant 2U19AI31541 awarded by the National Institutes of Health. The U.S. government therefore may have certain rights in this invention.

BACKGROUND OF THE INVENTION

The major histocompatability (MHC) class II molecules are expressed on the surfaces of antigen-presenting cells and B lymphocytes. By binding antigens and presenting the antigens to T cells, the MHC class II molecules are involved in triggering an immune response. Thus, the level of expression of the MHC class II molecules affects the induction of an immune response.

The genes which encode the α and β polypeptides of the MHC class II antigens are located at the HLA-D (histocompatability leukocyte antigen-D) region of the chromosome. Isotypes of the class II genes include those which are designated HLA-DR, HLA-DQ, and HLA-DP. Within these genes, there is substantial allelic polymorphism; for example, HLA-DR alleles include DR1, DR2, DR3, and DR4. In addition, subtypes of these alleles exist; for example, subtypes of DR4 include Dw4, Dw10, Dw13, Dw14, and Dw15.

Several autoimmune diseases are associated with expression of particular alleles of the MHC class II genes. For example, approximately 93% of patients afflicted with rheumatoid arthritis express HLA-DR1, HLA-DR4, or both (McDermott et al., Bulletin on the Rheumatic Diseases, 38:1–10). Other autoimmune diseases also are linked to expression of particular alleles. For example, Felty's syndrome, Sjogren's syndrome, systemic lupus erythematosus, and the development of toxicities to gold and penicillamine are associated with various HLA-DR alleles (McDermott et al., *Bulletin on the Rheumatic Diseases*, 38:1–10). As another example, pauciarticular juvenile rheumatoid arthritis is associated with HLA-PB2.1 (Begovich et al., 1989, PNAS 86:9489–9493). Approximately 70% of patients with insulin-dependent diabetes mellitus express HLA-DQ3.2B, DQA1, or DQB1, and susceptibility to the autoimmune dermatologic disease pemphigus vulgaris is linked to expression of HLA-DQB1.3 (Scharf et al., 1989, PNAS 86:6215–6219).

Activation of transcription of the MHC Class II genes has been shown to be dependent upon the transactivator CIITA (Steimle et al., 1993, Cell 75:135–146). CIITA does not function by directly binding DNA itself but rather by interacting with a conserved set of DNA binding proteins that associate with the class II promoter region (Steimle et al. (1994) *Science* 265:106–109; Chang et al. (1996) Immunity 4:167–178; Mach et al. (1996) *Annu. Rev. Immuno.* 14:301–331; Riley et al. (1995) *Immunity* 2:533–543). The transcriptional activation function of CIITA has been mapped to an amino terminal acidic domain (amino acids 26–137) (Zhou and Glimcher (1995) *Immunity* 2:545–553). The defect in a subset of MHC Class II deficient patients has been shown to be a mutation in CIITA, thereby demonstrating the importance of CIITA in regulating MHC Class II gene transcription (Steimle et al., 1993, *Cell* 75:135–146; Bontron et al. (1997) *Hum. Genet.* 99:541–546; Steimle et al. (1996) *Adv. Immunol.* 61:327–340). Given the critical role that CIITA plays in regulating MHC Class II gene expression, further information on how CIITA functions is of great interest.

SUMMARY OF THE INVENTION

This invention pertains to a protein that interacts with CIITA and enhances CIITA-regulated transcription from MHC class II gene promoters. A nucleic acid molecule encoding a protein that interacts with CIITA, termed CIITA-interacting protein 104 (also referred to herein as CIP104), has now been isolated and characterized. The CIP104-encoding nucleic acid was isolated based upon the ability of the encoded protein to interact with CIITA in a yeast two hybrid assay system. The nucleotide sequence of a cDNA encoding CIP104 and the predicted amino acid sequence of CIP104 have been determined and are shown in SEQ ID NOs: 1 and 2, respectively. Furthermore, CIP104 has been shown to enhance transcription from MHC class II promoters. This invention provides isolated compositions of CIP104 and isolated nucleic acid sequences encoding CIP104, as well as other compositions related thereto and methods of use thereof.

One aspect of the invention pertains to isolated nucleic acid molecules encoding CIP104, or fragments thereof. In one embodiment, the invention provides an isolated nucleic acid molecule comprising a nucleotide sequence encoding CIP104. In another embodiment, the invention provides an isolated nucleic acid molecule comprising a nucleotide sequence encoding a protein, wherein the protein comprises an amino acid sequence that is homologous to the amino acid sequence of SEQ ID NO: 2 and interacts with CIITA. In yet another embodiment, the invention provides an isolated nucleic acid molecule which hybridizes under stringent conditions to a nucleic acid molecule comprising the nucleotide sequence of SEQ ID NO: 1. In yet another embodiment, the invention provides an isolated nucleic acid molecule comprising the nucleotide sequence of SEQ ID NO: 1. In still other embodiments, the invention provides an isolated nucleic acid molecule encoding the amino acid sequence of SEQ ID NO: 2. Isolated nucleic acid molecules encoding CIP104 fusion proteins and isolated antisense nucleic acid molecules are also encompassed by the invention.

Another aspect of the invention pertains to vectors, such as recombinant expression vectors, containing an nucleic acid molecule of the invention and host cells into which such vectors have been introduced. In one embodiment, such a host cell is used to produce CIP104 by culturing the host cell in a suitable medium. If desired, CIP104 can be then isolated from the host cell or the medium.

Still another aspect of the invention pertains to isolated CIITA-interacting proteins, or portions thereof. In one embodiment, the invention provides an isolated CIP104 protein, or a portion thereof that interacts with CIITA. In yet another embodiment, the invention provides an isolated protein which comprises an amino acid sequence homologous to the amino acid sequence of SEQ ID NO: 2 and that interacts with CIITA. CIP104 fusion proteins are also encompassed by the invention.

The CIP104 proteins of the invention, or fragments thereof, can be used to prepare anti-CIP104 antibodies. Accordingly, the invention further provides antibodies that specifically binds CIP104. In one embodiment, the antibodies are polyclonal. In another embodiment, the antibodies are monoclonal. In yet another embodiment, the antibodies are labeled with a detectable substance.

The CIP104-encoding nucleic acid molecules of the invention can be used to prepare nonhuman transgenic animals that contain cells carrying a transgene encoding CIP104 or a portion of CIP104. Accordingly, such transgenic animals are also provided by the invention. In one embodiment, the CIP104 transgene carried by the transgenic animal alters an endogenous gene encoding endogenous CIP104 (e.g., a homologous recombinant animal).

Another aspect of the invention pertains to methods for detecting the presence of CIP104 activity (e.g., CIP104 protein or mRNA) in a biological sample. To detect CIP104 activity (e.g., protein or mRNA), the biological sample is contacted with an agent capable of detecting CIP104 protein (such as a labeled anti-CIP104 antibody) or CIP104 mRNA (such as a labeled nucleic acid probe capable of hybridizing to CIP104 mRNA) such that the presence of CIP104 protein or mRNA is detected in the biological sample.

Still another aspect of the invention pertains to methods for identifying compounds that modulate the activity or expression of CIP104 and methods for identifying compounds that modulate an interaction between CIP104 and CIITA. Screening methods for identifying proteins that interact with CIP are also encompassed by the invention.

DETAILED DESCRIPTION OF THE INVENTION

Figure 1:
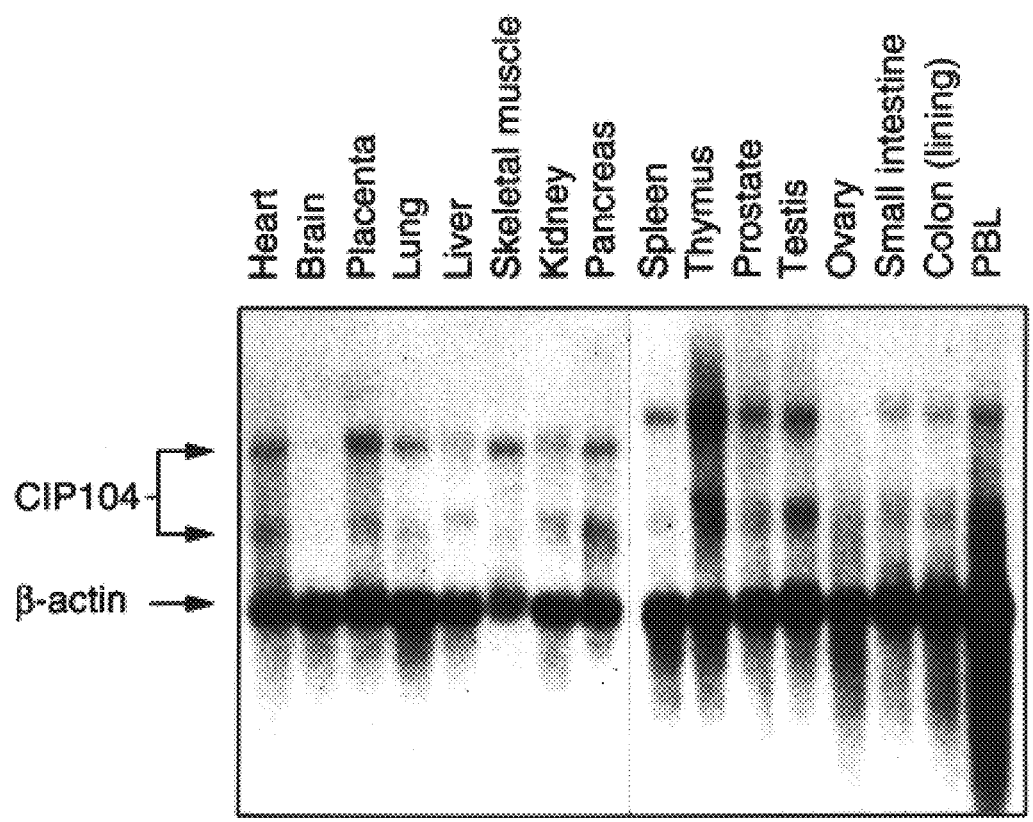
FIG. 1 is a photograph of a Northern hybridization filter probed with a CIP104-specific probe, depicting the tissue expression pattern of CIP104 mRNA in various tissues.

This invention pertains to a CIITA Interacting Protein 104 (CIP104), a protein that interacts with the MHC class II transcriptional transactivator CIITA. A cDNA encoding CIP104 was isolated based upon the interaction of CIP104 with the interaction domain of CIITA using a two-hybrid interaction trap assay in yeast (see Example 1). Expression of CIP104 mRNA in various tissue has been examined, with the highest level of expression observed in thymus (see Example 2). Functional studies showed that CIP104 enhances transactivation of MHC class II promoters by CIITA (see Example 3).

So that the invention may be more readily understood, certain terms are first defined.

As used herein, the term "CIP104" is intended to encompass proteins that share the distinguishing structural and functional features (described further herein) of the CIP104 protein of SEQ ID NO: 2.

As used herein, the term "CIITA" is intended to refer to the human MHC Class II transcriptional regulatory protein having the amino acid sequence described in Steimle et al. (1993) *Cell* 75:135–146, as well as the equivalent protein in other species (e.g., mouse CIITA).

As used herein, the term "nucleic acid molecule" is intended to include DNA molecules (e.g, cDNA or genomic DNA) and RNA molecules (e.g., mRNA). The nucleic acid molecule may be single-stranded or double-stranded, but preferably is double-stranded DNA.

An used herein, an "isolated nucleic acid molecule" refers to a nucleic acid molecule that is free of gene sequences which naturally flank the nucleic acid in the genomic DNA of the organism from which the nucleic acid is derived (i.e., genetic sequences that are located adjacent to the gene for the isolated nucleic molecule in the genomic DNA of the organism from which the nucleic acid is derived). For example, in various embodiments, an isolated CIP104 nucleic acid molecule typically contains less than about 10 kb of nucleotide sequences which naturally flank the nucleic acid molecule in genomic DNA of the cell from which the nucleic acid is derived, and more preferably contains less than about 5 kb, 4 kb, 3 kb, 2 kb, 1 kb, 0.5 kb or 0.1 kb of naturally flanking nucleotide sequences. An "isolated" CIP104 nucleic acid molecule may, however, be linked to other nucleotide sequences that do not normally flank the CIP104 sequences in genomic DNA (e.g., the CIP104 nucleotide sequences may be linked to vector sequences). In certain preferred embodiments, an "isolated" nucleic acid molecule, such as a cDNA molecule, also may be free of other cellular material. However, it is not necessary for the CIP104 nucleic acid molecule to be free of other cellular material to be considered "isolated" (e.g., a CIP104 DNA molecule separated from other mammalian DNA and inserted into a bacterial cell would still be considered to be "isolated").

As used herein, the term "hybridizes under high stringency conditions" is intended to describe conditions for hybridization and washing under which nucleotide sequences having substantial homology (e.g., typically greater than 70% homology) to each other remain stably hybridized to each other. A preferred, non-limiting example of high stringency conditions are hybridization in a hybridization buffer that contains 6× sodium chloride/sodium citrate (SSC) at a temperature of about 45° C. for several hours to overnight, followed by one or more washes in a washing buffer containing 0.2 ×SSC, 0.1% SDS at a temperature of about 50–65° C.

The term "homologous" as used in the context of amino acid sequences (e.g., when one amino acid sequence is said to be X% homologous to another amino acid sequence) is intended to encompass both amino acid identity and similarity between the two sequences. To determine the percent homology of two amino acid sequences, the sequences are aligned for optimal comparison purposes (e.g., gaps may be introduced in the sequence of one protein for optimal alignment with the other protein). The amino acid residues at corresponding amino acid positions are then compared and when a position in one sequence is occupied by the same or a similar amino acid residue as the corresponding position in the other sequence, then the molecules are homologous at that position. The percent homology between two sequences, therefore, is a function of the number of identical or similar positions shared by two sequences (i.e., % homology=# of identical or similar positions/total # of positions ×100). Computer algorithms known in the art can be used to optimally align the two amino acid sequences to be compared and to define similar amino acid residues. Preferably, the Basic Local Alignment Search Tool (BLAST) algorithm (described in Altschul, S. F. et al. (1990)

*J. Mol. Biol.* 215:403–410) is used to compare the two amino acid sequences to thereby determine the percent homology between the two sequences.

The term "homologous" as used in the context of nucleotide sequences (e.g., when one nucleotide sequence is said to be X% homologous to another nucleotide sequence) is intended to refer to nucleotide sequence identity between the two sequences. To determine the percent homology of two nucleotide sequences, the sequences are aligned for optimal comparison purposes (e.g., gaps may be introduced in the sequence of one nucleic acid molecule for optimal alignment with the other nucleic acid molecule). The nucleic acid bases at corresponding nucleotide positions are then compared and when a position in one sequence is occupied by the same nucleic acid base as the corresponding position in the other sequence, then the molecules are homologous at that position. The percent homology between two sequences, therefore, is a function of the number of identical positions shared by two sequences (ie., % homology=# of identical positions/total # of positions ×100). Computer algorithms known in the art can be used to optimally align the two nucleotide sequences to be compared. Preferably, the Basic Local Alignment Search Tool (BLAST) algorithm (described in Altschul, S. F. et al. (1990) *J. Mol. Biol.* 215:403–410) is used to compare the two nucleotide sequences to thereby determine the percent homology between the two sequences.

As used herein, a "naturally-occurring" nucleic acid molecule refers to an RNA or DNA molecule having a nucleotide sequence that occurs in nature (e.g., encodes a natural protein).

As used herein, an "antisense" nucleic acid comprises a nucleotide sequence which is complementary to a "sense" nucleic acid encoding a protein, e.g., complementary to the coding strand of a double-stranded cDNA molecule, complementary to an mRNA sequence or complementary to the coding strand of a gene. Accordingly, an antisense nucleic acid can hydrogen bond to a sense nucleic acid.

As used herein, the term "coding region" refers to regions of a nucleotide sequence comprising codons which are translated into amino acid residues, whereas the term "non-coding region" refers to regions of a nucleotide sequence that are not translated into amino acids (e.g., 5' and 3' untranslated regions).

As used herein, the term "vector" refers to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "recombinant expression vectors" or simply "expression vectors". In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

As used herein, the term "host cell" is intended to refer to a cell into which a nucleic acid of the invention, such as a recombinant expression vector of the invention, has been introduced. The terms "host cell" and "recombinant host cell" are used interchangeably herein. It should be understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

As used herein, a "transgenic animal" refers to a non-human animal, preferably a mammal, more preferably a mouse, in which one or more of the cells of the animal includes a "transgene". The term "transgene" refers to exogenous DNA which is integrated into the genome of a cell from which a transgenic animal develops and which remains in the genome of the mature animal, for example directing the expression of an encoded gene product in one or more cell types or tissues of the transgenic animal.

As used herein, a "homologous recombinant animal" refers to a type of transgenic non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

As used herein, an "isolated protein" refers to a protein that is substantially free of other proteins, cellular material and culture medium when isolated from cells or produced by recombinant DNA techniques, or chemical precursors or other chemicals when chemically synthesized.

As used herein, the term "antibody" is intended to include immunoglobulin molecules and immunologically active portions of immunoglobulin molecules, i.e., molecules that contain an antigen binding site which specifically binds (immunoreacts with) an antigen, such as Fab and $F(ab')_2$ fragments. The terms "monoclonal antibodies" and "monoclonal antibody composition", as used herein, refer to a population of antibody molecules that contain only one species of an antigen binding site capable of immunoreacting with a particular epitope of an antigen, whereas the term "polyclonal antibodies" and "polyclonal antibody composition" refer to a population of antibody molecules that contain multiple species of antigen binding sites capable of interacing with a particular antigen. A monoclonal antibody compositions thus typically display a single binding affinity for a particular antigen with which it immunoreacts.

There is a known and definite correspondence between the amino acid sequence of a particular protein and the nucleotide sequences that can code for the protein, as defined by the genetic code (shown below). Likewise, there is a known and definite correspondence between the nucleotide sequence of a particular nucleic acid molecule and the amino acid sequence encoded by that nucleic acid molecule, as defined by the genetic code.

| GENETIC CODE | |
|---|---|
| Alanine (Ala, A) | GCA, GCC, GCG, GCT |
| Arginine (Arg, R) | AGA, ACG, CGA, CGC, CGG, CGT |
| Asparagine (Asn, N) | AAC, AAT |
| Aspartic acid (Asp,D) | GAC, GAT |
| Cysteine (Cys, C) | TGC, TGT |
| Glutamic acid (Glu,E) | GAA, GAG |
| Glutamine (Gln, Q) | CAA, CAG |
| Glycine (Gly, G) | GGA, GGC, GGG, GGT |
| Histidine (His, H) | CAC, CAT |
| Isoleucine (Ile, I) | ATA, ATC, ATT |
| Leucine (Leu, L) | CTA, CTC, CTG, CTT, TTA, TTG |
| Lysine (Lys, K) | AAA, AAG |
| Methionine (Met, M) | ATG |
| Phenylalanine (Phe,F) | TTC, TTT |
| Proline (Pro, P) | CCA, CCC, CCG, CCT |
| Serine (Ser, S) | AGC, AGT, TCA, TCC, TCG, TCT |
| Threonine (Thr, T) | ACA, ACC, ACG, ACT |
| Tryptophan (Trp, W) | TGG |
| Tyrosine (Tyr, Y) | TAC, TAT |
| Valine (Val, V) | GTA, GTC, GTG, GTT |
| Termination signal (end) | TAA, TAG, TGA |

An important and well known feature of the genetic code is its redundancy, whereby, for most of the amino acids used to make proteins, more than one coding nucleotide triplet may be employed (illustrated above). Therefore, a number of different nucleotide sequences may code for a given amino acid sequence. Such nucleotide sequences are considered functionally equivalent since they result in the production of the same amino acid sequence in all organisms (although certain organisms may translate some sequences more efficiently than they do others). Moreover, occasionally, a methylated variant of a purine or pyrimidine may be found in a given nucleotide sequence. Such methylations do not affect the coding relationship between the trinucleotide codon and the corresponding amino acid.

In view of the foregoing, the nucleotide sequence of a DNA or RNA molecule coding for a CIP014 protein of the invention (or any portion thereof) can be use to derive the CIP104 amino acid sequence, using the genetic code to translate the DNA or RNA molecule into an amino acid sequence. Likewise, for any CIP104 amino acid sequence, corresponding nucleotide sequences that can encode the CIP104 protein can be deduced from the genetic code (which, because of its redundancy, will produce multiple nucleic acid sequences for any given amino acid sequence). Thus, description and/or disclosure herein of a CIP104 nucleotide sequence should be considered to also include description and/or disclosure of the amino acid sequence encoded by the nucleotide sequence. Similarly, description and/or disclosure of a CIP104 amino acid sequence herein should be considered to also include description and/or disclosure of all possible nucleotide sequences that can encode the amino acid sequence.

Various aspects of the invention are described in further detail in the following subsections:

I. Isolated Nucleic Acid Molecules

One aspect of the invention pertains to isolated nucleic acid molecules that encode CIP104, or fragments thereof. In a preferred embodiment, an isolated nucleic acid molecule of the invention comprises the nucleotide sequence shown in SEQ ID NO: 1. The sequence of SEQ ID NO: 1 corresponds to the human CIP104 cDNA. This cDNA comprises sequences encoding the CIP104 protein (i.e., "the coding region", from nucleotides 509–3343), as well as 5' untranslated sequences (nucleotides 1–508) and 3' untranslated sequences (nucleotides 3344–4236). Alternatively, the nucleic acid molecule may comprise only the coding region of SEQ ID NO: 1 (i.e., nucleotides 509–3343).

Moreover, the nucleic acid molecule of the invention can comprise only a portion of the coding region of SEQ ID NO: 1, for example a fragment encoding a biologically active portion of CIP104. The term "biologically active portion of CIP104" is intended to include portions of CIP104 that retain the ability to interact with CIITA. The ability of portions of CIP104 to interact with CIITA can be determined in standard in vitro interaction assays, for example using a CIITA fusion protein that comprises the interaction domain of CIITA that interacts with CIP104. Nucleic acid fragments encoding biologically active portions of CIP104 can be prepared by isolating a portion of SEQ ID NO: 1, expressing the encoded portion of CIP104 protein or peptide (e.g., by recombinant expression in a host cell) and assessing the ability of the portion to interact with CIITA, for example using a glutathione-S-transferase (GST)-CIITA fusion protein.

In certain embodiments, an isolated nucleic acid fragment of the invention is at least 30 nucleotides in length. More preferably the fragment is at least 50, 100, 200, 300, 400, 500, 600, 700, 800, 900 or 1000 nucleotides in length. In preferred embodiments, an isolated nucleic acid fragment of the invention comprises at least 30 contiguous nucleotides of SEQ ID NO: 1, more preferably at least 50, 100, 200, 300, 400, 500, 600, 700, 800, 90, 1000, 2000 or 3000 contiguous nucleotides of SEQ ID NO: 1.

The invention further encompasses nucleic acid molecules that differ from SEQ ID NO: 1 (and fragments thereof) due to degeneracy of the genetic code and thus encode the same CIP104 protein as that encoded by SEQ ID NO: 1. Accordingly, in another embodiment, an isolated nucleic acid molecule of the invention has a nucleotide sequence encoding a protein having an amino acid sequence shown in SEQ ID NO: 2. Moreover, the invention encompasses nucleic acid molecules that encode portions of SEQ ID NO: 2, such as biologically active portions thereof.

A nucleic acid molecule having the nucleotide sequence of SEQ ID NO: 1, or a portion thereof, can be isolated using standard molecular biology techniques and the sequence information provided herein. For example, a CIP104 cDNA can be isolated from a cDNA library using all or portion of SEQ ID NO: 1 as a hybridization probe and standard hybridization techniques (e.g., as described in Sambrook, J., et al. *Molecular Cloning: A Laboratory Manual*. 2nd, ed., Cold Spring Harbor Laboratory, Cold Spring Harbor, N.Y., 1989). Moreover, a nucleic acid molecule encompassing all or a portion of SEQ ID NO: 1 can be isolated by the polymerase chain reaction using oligonucleotide primers designed based upon the sequence of SEQ ID NO: 1. For example, mRNA can be isolated from cells (e.g., by the guanidinium-thiocyanate extraction procedure of Chirgwin et al. (1979) *Biochemistry* 18: 5294–5299) and cDNA can be prepared using reverse transcriptase (e.g., Moloney MLV reverse transcriptase, available from Gibco/BRL, Bethesda, MD; or AMV reverse transcriptase, available from Seikagaku America, Inc., St. Petersburg, Fla.). Synthetic oligonucleotide primers for PCR amplification can be designed based upon the nucleotide sequence shown in SEQ ID NO: 1. A nucleic acid of the invention can be amplified using cDNA or, alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to a CIP104 nucleotide sequence can be prepared by standard synthetic techniques, e.g., using an automated DNA synthesizer.

In addition to the CIP104 nucleotide sequence shown in SEQ ID NO: 1, it will be appreciated by those skilled in the art that DNA sequence polymorphisms that lead to changes in the amino acid sequences of CIP104 may exist within a population. Such genetic polymorphism in the CIP104 gene may exist among individuals within a population due to natural allelic variation. Such natural allelic variations can typically result in 1–5% variance in the nucleotide sequence of the a gene. Any and all such nucleotide variations and resulting amino acid polymorphisms in CIP104 that are the result of natural allelic variation and that do not alter the functional activity of CIP104 are intended to be within the scope of the invention. Moreover, nucleic acid molecules encoding CIP104 proteins from other species, and thus which have a nucleotide sequence that differs from the human sequence of SEQ ID NO: 1 but that is related to the human sequence, are intended to be within the scope of the invention.

Nucleic acid molecules corresponding to natural allelic variants and nonhuman homologues of the human CIP104 cDNAs of the invention can be isolated based on their homology to the human CIP104 nucleic acid molecules disclosed herein using the human cDNA, or a portion thereof, as a hybridization probe according to standard hybridization techniques under high stringency hybridization conditions. Accordingly, in another embodiment, an isolated nucleic acid molecule of the invention hybridizes under high stringency conditions to a second nucleic acid molecule comprising the nucleotide sequence of SEQ ID NO: 1. In certain embodiment, the isolated nucleic acid molecule comprises at least 30, 50, 100, 200, 300, 400, 500, 600, 700, 800, 900, 1000, 2000 or 3000 contiguous nucleotides of SEQ ID NO: 1. Preferably, an isolated nucleic acid molecule of the invention that hybridizes under high stringency conditions to the sequence of SEQ ID NO: 1 corresponds to a naturally-occurring nucleic acid molecule. In on embodiment, the nucleic acid encodes a natural human CIP104 protein. In another embodiment, the nucleic acid molecule encodes a natural murine homologue of a human CIP104 protein, such as mouse CIP104 protein.

In addition to naturally-occurring allelic variants of the CIP104 sequence that may exist in the population, the skilled artisan will further appreciate that changes may be introduced by mutation into the nucleotide sequence of SEQ ID NO: 1, thereby leading to changes in the amino acid sequence of the encoded protein, without altering the functional activity of the CIP104 protein. For example, nucleotide substitutions leading to amino acid substitutions at "non-essential" amino acid residues may be made in the sequence of SEQ ID NO: 1. A "non-essential" amino acid residue is a residue that can be altered from the wild-type sequence of CIP104 (e.g., the sequence of SEQ ID NO: 2) without altering the functional activity of CIP104, such as its ability to interact with CIITA or its ability to enhance transcription from MHC class II promoters, whereas an "essential" amino acid residue is required for functional activity.

Accordingly, another aspect of the invention pertains to nucleic acid molecules encoding CIP104 proteins that contain changes in amino acid residues that are not essential for CIP104 activity. Such CIP104 proteins differ in amino acid sequence from SEQ ID NO: 2 yet retain CIP104 activity. In one embodiment, the isolated nucleic acid molecule comprises a nucleotide sequence encoding a protein, wherein the protein comprises an amino acid sequence at least 60% homologous to the amino acid sequence of SEQ ID NO: 2 and interacts with CIITA or enhances transcription from MHC class II promoters. Preferably, the protein encoded by the nucleic acid molecule is at least 70% homologous to SEQ ID NO: 2, more preferably at least 80% homologous to SEQ ID NO: 2, even more preferably at least 90% homologous to SEQ ID NO: 2, and most preferably at least 95% homologous to SEQ ID NO: 2.

In another embodiment, the isolated nucleic acid molecule comprises a nucleotide sequence at least 60% homologous to the nucleotide sequence of SEQ ID NO: 1 and encodes a protein that interacts with CIITA or enhances transcription from MHC class II promoters. Preferably, the nucleotide sequence is at least 70% homologous to SEQ ID NO: 1, more preferably at least 80% homologous to SEQ ID NO: 1, even more preferably at least 90% homologous to SEQ ID NO: 1, and most preferably at least 95% homologous to SEQ ID NO: 1.

The percent homology between two amino acid sequences (e.g., SEQ ID NO: 2 and a variant form thereof) or between two nucleotide sequences (e.g., SEQ ID NO: 1 and a variant form thereof) can be determined as described above in the definition section for homology.

An isolated nucleic acid molecule encoding a CIITA-interacting protein homologous to the protein of SEQ ID NO: 2 can be created by introducing one or more nucleotide substitutions, additions or deletions into the nucleotide sequence of SEQ ID NO: 1 such that one or more amino acid substitutions, additions or deletions are introduced into the encoded protein. Mutations can be introduced into SEQ ID NO: 1 by standard techniques, such as site-directed mutagenesis and PCR-mediated mutagenesis. Preferably, conservative amino acid substitutions are made at one or more non-essential amino acid residues. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in CIP104 is preferably replaced with another amino acid residue from the same side chain family. Alternatively, in another embodiment, mutations can be introduced randomly along all or part of the CIP104 coding sequence, such as by saturation mutagenesis, and the resultant mutants can be screened for their ability to interact with CIITA (e.g., using a GST-CIITA fusion protein) to identify mutants that retain CIITA-interacting ability.

Following mutagenesis of SEQ ID NO: 1, the encoded mutant protein can be expressed recombinantly in a host cell and the ability of the mutant protein to interact with CIITA can be determined using an in vitro interaction assay. For example, a recombinant CIP104 (e.g., a mutated or truncated form of SEQ ID NO: 2) can be radiolabeled and incubated with a GST-CIITA fusion protein. Glutathione-sepharose beads are then added to the mixture to precipitate the CIP104-CIITA-GST complex, if such a complex is formed. After washing the beads to remove non-specific binding, the amount of radioactive protein associated with the beads is determined and compared to the amount of radioactive protein remaining in the eluate to thereby determine whether the mutant CIP104 is capable of interacting with CIITA.

Another aspect of the invention pertains to isolated nucleic acid molecules that are related to the CIP104 nucleic acid molecule disclosed herein and that are obtainable using processes that utilize the nucleic acid molecules, or portions thereof, disclosed herein. For example, the invention provides an isolated nucleic acid molecule obtainable by a process comprising:

(a) contacting a sample population of nucleic acid molecules with at least one probe/primer encoding an amino acid sequence shown in SEQ ID NO: 2, said probe/primer being at least 15 nucleotides in length;

(b) isolating or amplifying nucleic acid molecules within the sample population that hybridize to said probe/primer to thereby obtain a selected population of nucleic acid molecules;

(c) determining the nucleotide sequences of nucleic acid molecules within the selected population; and (d) isolating a nucleic acid molecule from the selected population that is at least 1000 nucleotides in length and whose nucleotide sequence is at least 60% homologous to the nucleotide sequence of SEQ ID NO: 1.

In alternative embodiments, step (d) comprises selecting a nucleic acid molecule within the selected population that is at least 1000 nucleotides in length and whose nucleotide sequence is at least 70%, 80%, 90% or 95% homologous to the nucleotide sequence of SEQ ID NO: 1. In other embodiments, the probe/primer can be at least 20, 25, 30, 35, 40, 50, 100, 200, 300, 400, 500, 600, 700, 800, 900 or 1000 nucleotides in length.

The invention also provides an isolated nucleic acid molecule obtainable by a process comprising:

(a) contacting a sample population of nucleic acid molecules with a probe comprising at least 30 contiguous nucleotides of SEQ ID NO: 1;

(b) isolating nucleic acid molecules within the sample population that hybridize to said probe/primer under high stringency conditions to thereby obtain a selected population of nucleic acid molecules;

(c) determining the nucleotide sequence of nucleic acid molecules within the selected population; and (d) isolating a nucleic acid molecule from the selected population that is at least 1000 nucleotides in length and whose nucleotide sequence is at least 60% homologous to the nucleotide sequence of SEQ ID NO: 1.

In alternative embodiments, step (d) comprises selecting a nucleic acid molecule within the selected population that is at least 1000 nucleotides in length and whose nucleotide sequence is at least 70%, 80%, 90% or 95% homologous to the nucleotide sequence of SEQ ID NO: 1. In other alternative embodiments, the probe used in step (a) comprises at least 50, 100, 200, 300, 400, 500, 600, 700, 800, 900 or 1000 contiguous nucleotides of SEQ ID NO: 1.

The invention still further provides an isolated nucleic acid molecule obtainable by a process comprising:

(a) contacting a sample population of nucleic acid molecules with a first and a second primer, wherein at least one of the first and second primers is a degenerate oligonucleotide primer comprising a nucleotide sequence encoding an amino acid sequence shown in SEQ ID NO: 2, said first and second primers being at least 15 nucleotides in length;

(b) amplifying nucleic acid molecules within the sample population that hybridize to said first and second primer using a polymerase chain reaction to thereby obtain a selected population of nucleic acid molecules;

(c) determining the nucleotide sequence of nucleic acid molecules within the selected population; and (d) isolating a nucleic acid molecule within the selected population that is at least 1000 nucleotides in length and whose nucleotide sequence is at least 60% homologous to the entire nucleotide sequence of SEQ ID NO: 1.

In alternative embodiments, step (d) comprises selecting a nucleic acid molecule within the selected population that is at least 1000 nucleotides in length and whose nucleotide sequence is at least 70%, 80%, 90% or 95% homologous to the nucleotide sequence of SEQ ID NO: 1. In other alternative embodiments, first and/or second primers used in step (a) are at least 20, 25, 30, 35, 40 or 50 nucleotides in length.

In preferred embodiments, the degenerate oligonucleotide primer encodes an amino sequence shown within about amino acid positions 1–20 of SEQ ID NO: 2 (i.e., the amino terminal end of SEQ ID NO: 2). In another preferred embodiment, the degenerate oligonucleotide primer encodes an amino sequence shown within about amino acid positions 925–945 of SEQ ID NO: 2 (i.e., the carboxy terminal end of SEQ ID NO: 2). In a preferred embodiment, both the first and second primers used in the process are degenerate oligonucleotide primers encoding sequences shown in SEQ ID NO: 2, preferably wherein the first primer encodes a sequence at the amino terminal end of SEQ ID NO: 2 and the second primer encodes a sequence at the carboxy terminal end of SEQ ID NO: 2. In another embodiment, the first and/or second primers have a nucleotide sequence found at the 5' end of SEQ ID NO: 1 (e.g., within the first 60 nucleotides of SEQ ID NO: 1) or a nucleotide sequence found at the 3' end of SEQ ID NO: 1 (e.g., within the last 60 nucleotides of SEQ ID NO: 1). In a preferred embodiment, the first primer has a nucleotide sequence from the 5' end of SEQ ID NO: 1 (e.g., within the first 60 nucleotides) and the second primer has a nucleotide sequence from the 3' end of SEQ ID NO: 1 (e.g., within the last 60 nucleotides).

Probes/primers to be used in the above-described processes can be prepared based on the nucleotide sequences provided herein using standard molecular biology techniques. The sample population of nucleic acid molecules used in step (b) of the processes can be, for example, a pool of mRNAs, a cDNA library or a genomic DNA library, which can be prepared according to standard molecular biology techniques. Hybridization of a probe to the sample population and isolation of molecules that hybridize under high stringency conditions can be performed as described hereinbefore and using hybridization methods well known in the art. Similarly, amplification of sequences within the sample population using first and second primers can be performed as described hereinbefore and using PCR methods well known in the art. In situations where only one of the first and second primers is derived from SEQ ID NO: 2 (or SEQ ID NO: 1), the other primer is a "docking" primer that is complimentary to a fixed sequence within the sample population, such as an oligo dT primer or a primer that hybridizes to fixed vector sequences within the sample population. Preferred PCR methods for use in the processes include 5'- and 3'-RACE.

The nucleotide sequences of the nucleic acid molecules within the selected population can be determined by, for example, dideoxynucleotide sequencing (manual or automated) or other well known techniques for DNA sequencing. Finally, the degree of homology between nucleotide sequences within the selected population and either SEQ ID NO: 1 can be determined as described hereinbefore to thus allow for isolation of nucleic acid molecules related to SEQ ID NO: 1.

Another aspect of the invention pertains to isolated nucleic acid molecules that are antisense to the coding strand of a CIP104 mRNA or gene. An antisense nucleic acid of the invention can be complementary to an entire CIP104 coding strand, or to only a portion thereof. In one embodiment, an antisense nucleic acid molecule is antisense to a coding region of the coding strand of a nucleotide sequence encoding CIP104 (e.g., the coding region of SEQ ID NO: 1 comprises nucleotides 509–3343). In another embodiment, the antisense nucleic acid molecule is antisense to a noncoding region of the coding strand of a nucleotide sequence encoding CIP104. In certain embodiments, an antisense nucleic acid of the invention is at least 300, nucleotides in length. More preferably, the antisense nucleic acid is at least 400, 500, 600, 700, 800, 900 or 1000 nucleotides in length. In preferred embodiments, an antisense of the invention comprises at least 30 contiguous nucleotides of the noncoding strand of SEQ ID NO: 1, more preferably at least 50, 100, 200, 300, 400, 500, 600, 700, 800, 900 or 1000 contiguous nucleotides of the noncoding strand of SEQ ID NO: 1.

Given the coding strand sequences encoding CIP104 disclosed herein (e.g., SEQ ID NO: 1), antisense nucleic acids of the invention can be designed according to the rules of Watson and Crick base pairing. The antisense nucleic acid molecule may be complementary to the entire coding region of CIP104 mRNA, or alternatively can be an oligonucleotide which is antisense to only a portion of the coding or noncoding region of CIP104 mRNA. For example, the antisense oligonucleotide may be complementary to the region surrounding the translation start site of CIP104 mRNA. An antisense oligonucleotide can be, for example, about 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

In another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. A ribozyme having specificity for a CIP104-encoding nucleic acid can be designed based upon the nucleotide sequence of a CIP104 cDNA disclosed herein (i.e., SEQ ID NO: 1). For example, a derivative of a Tetrahymena L-19 IVS RNA can be constructed in which the base sequence of the active site is complementary to the base sequence to be cleaved in a CIP104-encoding mRNA. See for example Cech et al. U.S. Pat. No. 4,987,071; and Cech et al. U.S. Pat. No. 5,116,742. Alternatively, CIP104 mRNA can be used to select a catalytic RNA having a specific ribonuclease activity from a pool of RNA molecules. See for example Bartel, D. and Szostak, J. W. (1993) Science 261: 1411–1418.

Yet another aspect of the invention pertains to isolated nucleic acid molecules encoding CIP104 fusion proteins. Such nucleic acid molecules, comprising at least a first nucleotide sequence encoding a CIP104 protein, polypeptide or peptide operatively linked to a second nucleotide sequence encoding a non-CIP104 protein, polypeptide or peptide, can be prepared by standard recombinant DNA techniques. CIP104 fusion proteins are described in further detail below in subsection III.

II. Recombinant Expression Vectors and Host Cells

Another aspect of the invention pertains to vectors, preferably recombinant expression vectors, containing a nucleic acid encoding CIP104 (or a portion thereof). The expression vectors of the invention comprise a nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to includes promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cell and those which direct expression of the nucleotide sequence only in certain host cells (e.g., tissue-specific regulatory sequences). It will be appreciated by those skilled in the art that the design of the expression vector may depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein (e.g., CIP104 proteins, mutant forms of CIP104 proteins, CIP104 fusion proteins and the like).

The recombinant expression vectors of the invention can be designed for expression of CIP104 protein in prokaryotic or eukaryotic cells. For example, CIP104 can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector may be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors can serve one or more purposes: 1) to increase expression of recombinant protein; 2) to increase the solubility of the recombinant protein; 3) to aid in the purification of the recombinant protein by acting as a ligand in affinity purification; 4) to provide an epitope tag to aid in detection and/or purification of the protein; and/or 5) to provide a marker to aid in detection of the protein (e.g., a color marker using β-galactosidase fusions). Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc.; Smith, D. B. and Johnson, K.S. (1988) *Gene* 67:31–40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Recombinant proteins also can be expressed in eukaryotic cells as fusion proteins for the same purposes discussed above.

Examples of suitable inducible non-fusion *E. coli* expression vectors include pTrc (Amann et al., (1988) *Gene* 69:301–315) and pET 11d (Studier et al., *Gene Expression Technology: Methods in Enzymology* 185, Academic Press, San Diego, Calif. (1990) 60–89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS174 (DE3) from a resident λ prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119–128). Another strategy is to alter the nucleic acid sequence of the nucleic acid to be inserted into an expression vector so that the individual codons for each amino acid are those preferentially utilized in *E. coli* (Wada et al., (1992) *Nuc. Acids Res.* 20:2111–2118). Such alteration of nucleic acid sequences of the invention can be carried out by standard DNA synthesis techniques.

In another embodiment, the CIP104 expression vector is a yeast expression vector. Examples of vectors for expression in yeast *S. cerivisae* include pYepSec1 (Baldari. et al., (1987) *EMBO J.* 6:229–234), pMFa (Kurjan and Herskowitz, (1982) *Cell* 30:933–943), pJRY88 (Schultz et al., (1987) *Gene* 54:113–123), and pYES2 (Invitrogen Corporation, San Diego, Calif.).

Alternatively, CIP104 can be expressed in insect cells using baculovirus expression vectors. Baculovirus vectors available for expression of proteins in cultured insect cells (e.g., Sf 9 cells) include the pAc series (Smith et al., (1983) *Mol. Cell Biol.* 3:2156–2165) and the pVL series (Lucklow, V. A., and Summers, M. D., (1989) Virology 170:31–39).

In yet another embodiment, a nucleic acid of the invention is expressed in mammalian cells using a mammalian expression vector. Examples of mammalian expression vectors include pMex-NeoI, pCDM8 (Seed, B., (1987) Nature 329:840) and pMT2PC (Kaufman et al. (1987), EMBO J. 6:187–195). When used in mammalian cells, the expression vector's control functions are often provided by viral regulatory elements. For example, commonly used promoters are derived from polyoma, Adenovirus 2, cytomegalovirus and Simian Virus 40.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include lymphoid-specific promoters (Calame and Eaton (1988) *Adv. Immunol.* 43:235–275), in particular promoters of T cell receptors (Winoto and Baltimore (1989) *EMBO J.* 8:729–733) and immunoglobulins (Banerji et al. (1983) *Cell* 33:729–740; Queen and Baltimore (1983) *Cell* 33:741–748), the albumin promoter (liver-specific; Pinkert et al. (1987) *Genes Dev.* 1:268–277), neuron-specific promoters (e.g., the neurofilament promoter; Byrne and Ruddle (1989) *Proc. Natl. Acad. Sci. USA* 86:5473–5477), pancreas-specific promoters (Edlund et al. (1985) *Science* 230:912–916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374–379) and the α-fetoprotein promoter (Campes and Tilghman (1989) *Genes Dev.* 3:537–546).

Moreover, inducible regulatory systems for use in mammalian cells are known in the art, for example systems in which gene expression is regulated by heavy metal ions (see e.g., Mayo et al. (1982) *Cell* 29:99–108; Brinster et al. (1982) *Nature* 296:39–42; Searle et al. (1985) *Mol. Cell. Biol.* 5:1480–1489), heat shock (see e.g., Nouer et al. (1991) in *Heat Shock Response*, e.d. Nouer, L., CRC, Boca Raton, Fla., pp167–220), hormones (see e.g., Lee et al. (1981) *Nature* 294:228–232; Hynes et al. (1981) *Proc. Natl. Acad. Sci. USA* 78:2038–2042; Klock et al. (1987) *Nature* 329:734–736; Israel & Kaufman (1989) *Nucl. Acids Res.* 17:2589–2604; and PCT Publication No. WO 93/23431), FK506-related molecules (see e.g., PCT Publication No. WO 94/18317) or tetracyclines (Gossen, M. and Bujard, H. (1992) *Proc. Natl. Acad. Sci. USA* 89:5547–5551; Gossen, M. et al. (1995) *Science* 268:1766–1769; PCT Publication No. WO 94/29442; and PCT Publication No. WO 96/01313). Accordingly, in another embodiment, the invention provides a recombinant expression vector in which CIP104 DNA is operatively linked to an inducible eukaryotic promoter, thereby allowing for inducible expression of CIP104 protein in eukaryotic cells.

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to CIP104 mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to recombinant host cells into which a vector, preferably a recombinant expression vector, of the invention has been introduced. A host cell may be any prokaryotic or eukaryotic cell. For example, CIP104 protein may be expressed in bacterial cells such as *E. coli*, insect cells, yeast or mammalian cells (such as Chinese hamster ovary cells (CHO) or COS cells). Other suitable host cells are known to those skilled in the art. Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook et al. (*Molecular Cloning: A Laboratory Manual*, 2nd Edition, Cold Spring Harbor Laboratory press (1989)), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker may be introduced into a host cell on the same vector as that encoding CIP104 or may be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) CIP104 protein. Accordingly, the invention further provides methods for producing CIP104 protein using the host cells of the invention. In one embodiment, the method comprises culturing the host cell of invention (into which a recombinant expression vector encoding CIP104 has been introduced) in a suitable medium until CIP104 is produced. In another embodiment, the method further comprises isolating CIP104 from the medium or the host cell. In its native form the CIP104 protein is an intracellular protein and, accordingly, recombinant CIP104 protein can be expressed intracellularly in a recombinant host cell and then isolated from the host cell, e.g., by lysing the host cell and recovering the recombinant CIP104 protein from the lysate. Alternatively, recombinant CIP104 protein can be prepared as a extracellular protein by operatively linking a heterologous signal sequence to the amino-terminus of the protein such that the protein is secreted from the host cells. In this case, recombinant CIP104 protein can be recovered from the culture medium in which the cells are cultured.

Certain host cells of the invention can also be used to produce nonhuman transgenic animals. For example, in one embodiment, a host cell of the invention is a fertilized oocyte or an embryonic stem cell into which CIP104-coding sequences have been introduced. Such host cells can then be used to create non-human transgenic animals in which. exogenous CIP104 sequences have been introduced into their genome or homologous recombinant animals in which endogenous CIP104 sequences have been altered. Such animals are useful for studying the function and/or activity of CIP104 and for identifying and/or evaluating modulators of CIP104 activity. Accordingly, another aspect of the invention pertains to nonhuman transgenic animals which contain cells carrying a transgene encoding a CIP104 protein or a portion of a CIP104 protein. In a subembodiment, of the transgenic animals of the invention, the transgene alters an endogenous gene encoding an endogenous CIP104 protein (e.g., homologous recombinant animals in which the endogenous CIP104 gene has been functionally disrupted or "knocked out", or the nucleotide sequence of the endogenous CIP104 gene has been mutated or the transcriptional regulatory region of the endogenous CIP104 gene has been altered).

A transgenic animal of the invention can be created by introducing CIP104-encoding nucleic acid into the male pronuclei of a fertilized oocyte, e.g., by microinjection, and allowing the oocyte to develop in a pseudopregnant female foster animal. The human CIP104 cDNA sequence of SEQ ID NO: 1 can be introduced as a transgene into the genome of a non-human animal. Alternatively, a nonhuman homologue of the human CIP104 gene, such as a mouse CIP104 gene, can be isolated based on hybridization to the human CIP104 cDNA and used as a transgene. Intronic sequences and polyadenylation signals can also be included in the transgene to increase the efficiency of expression of the transgene. A tissue-specific regulatory sequence(s) can be operably linked to the CIP104 transgene to direct expression of CIP104 protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the CIP104 transgene in its genome and/or expression of CIP104 mRNA in tissues or cells of the animals. A transgenic founder animal can then be used to breed additional animals carrying the transgene. Moreover, transgenic animals carrying a transgene encoding CIP104 can further be bred to other transgenic animals carrying other transgenes.

To create a homologous recombinant animal, a vector is prepared which contains at least a portion of a CIP104 gene into which a deletion, addition or substitution has been introduced to thereby alter, e.g., functionally disrupt, the endogenous CIP104 gene. The CIP104 gene may be a human gene (e.g., from a human genomic clone isolated from a human genomic library screened with the cDNA of SEQ ID NO: 1), but more preferably, is a non-human homologue of a human CIP104 gene. For example, a mouse CIP104 gene can be isolated from a mouse genomic DNA library using the human CIP104 cDNA of SEQ ID NO: 1 as a probe. The mouse CIP104 gene then can be used to construct a homologous recombination vector suitable for altering an endogenous CIP104 gene in the mouse genome. In a preferred embodiment, the vector is designed such that, upon homologous recombination, the endogenous CIP104 gene is functionally disrupted (i.e., no longer encodes a functional protein; also referred to as a "knock out" vector). Alternatively, the vector can be designed such that, upon homologous recombination, the endogenous CIP104 gene is mutated or otherwise altered but still encodes functional protein (e.g., the upstream regulatory region can be altered to thereby alter the expression of the endogenous CIP104 protein). In the homologous recombination vector, the altered portion of the CIP104 gene is flanked at its 5' and 3' ends by additional nucleic acid of the CIP104 gene to allow for homologous recombination to occur between the exogenous CIP104 gene carried by the vector and an endogenous CIP104 gene in an embryonic stem cell. The additional flanking CIP104 nucleic acid is of sufficient length for successful homologous recombination with the endogenous gene. Typically, several kilobases of flanking DNA (both at the 5' and 3' ends) are included in the vector (see e.g., Thomas, K. R. and Capecchi, M. R. (1987) *Cell* 51:503 for a description of homologous recombination vectors). The vector is introduced into an embryonic stem cell line (e.g., by electroporation) and cells in which the introduced CIP104 gene has homologously recombined with the endogenous CIP104 gene are selected (see e.g., Li, E. et al. (1992) *Cell* 69:915). The selected cells are then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113–152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination vectors and homologous recombinant animals are described further in Bradley, A. (1991) *Current Opinion in Biotechnology* 2:823–829 and in PCT International Publication Nos.: WO 90/11354 by Le Mouellec et al.; WO 91/01140 by Smithies et al.; WO 92/0968 by Zijlstra et al.; and WO 93/04169 by Berns et al.

In addition to the foregoing, the skilled artisan will appreciate that other approaches known in the art for homologous recombination can be applied to the instant invention. Enzyme-assisted site-specific integration systems are known in the art and can be applied to integrate a DNA molecule at a predetermined location in a second target DNA molecule. Examples of such enzyme-assisted integration systems include the Cre recombinase-lox target system (e.g., as described in Baubonis, W. and Sauer, B. (1993) *Nucl. Acids Res*. 21:2025–2029; and Fukushige, S. and Sauer, B. (1992) *Proc. Natl. Acad. Sci. USA* 89:7905–7909) and the FLP recombinase-FRT target system (e.g., as described in Dang, D. T. and Perrimon, N. (1992) *Dev. Genet*. 13:367–375; and Fiering, S. et al. (1993) *Proc. Natl. Acad. Sci. USA* 90:8469–8473). Tetracycline-regulated inducible homologous recombination systems, such as described in PCT Publication No. WO 94/29442 and PCT Publication No. WO 96/01313, also can be used.

III. Isolated CIP104 Proteins and Anti-CIP104 Antibodies

Another aspect of the invention pertains to isolated CIP104 proteins, and portions thereof, such as biologically active portions, as well as peptide fragments suitable as immunogens to raise anti-CIP104 antibodies. In one embodiment, the invention provides an isolated preparation of CIP104 protein. Preferably, the CIP104 protein has an amino acid sequence shown in SEQ ID NO: 2. In other embodiments, the CIP104 protein is substantially homologous to SEQ ID NO: 2 and retains the functional activity of the protein of SEQ ID NO: 2 yet differs in amino acid sequence due to natural allelic variation or mutagenesis, or is a mammalian homologue of the protein of SEQ ID NO: 2 (e.g., a human homologue), as described in detail in subsection I above. Accordingly, in another embodiment, the CIP104 protein is a protein which comprises an amino acid sequence at least 60% homologous to the amino acid sequence of SEQ ID NO: 2 and that interacts with CIITA or enhances transcription from MHC class II promoters. Preferably, the protein is at least 70% homologous to SEQ ID NO: 2, more preferably at least 80% homologous to SEQ ID NO: 2, even more preferably at least 90% homologous to SEQ ID NO: 2, and most preferably at least 95% homologous to SEQ ID NO: 2.

In other embodiments, the invention provides isolated portions of the CIP104 protein. For example, the invention further encompasses a portion of a CIP104 protein that interacts with CIITA. As demonstrated in the examples, CIP104 protein interacts with the interation domain of CIITA (about amino acid positions 134 to 317 of CIITA). An in vitro interaction assay (such as that described above in subsection I utilizing a GST-CIITA fusion protein comprising the interaction domain of CIITA) can be used to determine the ability of CIP104 peptide fragments to interact with the interaction domian of CIITA to thereby identify peptide fragments that interact with CIITA.

CIP104 proteins are preferably produced by recombinant DNA techniques. For example, a nucleic acid molecule encoding the protein is cloned into an expression vector (as described above), the expression vector is introduced into a host cell (as described above) and the CIP104 protein is expressed in the host cell. The CIP104 protein can then be isolated from the cells by an appropriate purification scheme using standard protein purification techniques. Alternative to recombinant expression, a CIP104 polypeptide can be synthesized chemically using standard peptide synthesis techniques. Moreover, native CIP104 protein can be isolated from cells (e.g., from T cells), for example by immunoprecipitation using an anti-CIP104 antibody.

The invention also provides CIP104 fusion proteins. As used herein, a CIP104 "fusion protein" comprises a CIP104 polypeptide operatively linked to a non-CIP104 polypeptide. A "CIP104 polypeptide" refers to a polypeptide having an amino acid sequence corresponding to CIP104 protein, or a peptide fragment thereof, whereas a "non-CIP104 polypeptide" refers to a polypeptide having an amino acid sequence corresponding to another protein. Within the fusion protein, the term "operatively linked" is intended to indicate that the CIP104 polypeptide and the non-CIP104 polypeptide are fused in-frame to each other. The non-CIP104 polypeptide may be fused to the N-terminus or C-terminus of the CIP104 polypeptide. For example, in one embodiment, the fusion protein is a GST-CIP104 fusion protein in which the CIP104 sequences are fused to the C-terminus of the GST sequences. In another embodiment, the fusion protein is a CIP104-HA fusion protein in which the CIP104 nucleotide sequence is inserted in a vector such as pCEP4-HA vector (Herrscher, R. F. et al. (1995) *Genes Dev*. 9:3067–3082) such that the CIP104 sequences are fused in frame to an influenza hemagglutinin epitope tag. Such fusion proteins can facilitate the purification of recombinant CIP104.

Preferably, a CIP104 fusion protein of the invention is produced by standard recombinant DNA techniques. For example, DNA fragments coding for the different polypeptide sequences are ligated together in-frame in accordance with conventional techniques, for example employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g. a GST polypeptide or an HA epitope tag). A CIP104-encoding nucleic acid can be cloned into such an expression vector such that the fusion moiety is linked in-frame to the CIP104 protein.

An isolated CIP104 protein, or fragment thereof, can be used as an immunogen to generate antibodies that bind CIP104 using standard techniques for polyclonal and monoclonal antibody preparation. The CIP104 protein can be used to generate antibodies or, alternatively, an antigenic peptide fragment of CIP104 can be used as the immunogen. An antigenic peptide fragment of CIP104 typically comprises at least 8 amino acid residues of the amino acid sequence shown in SEQ ID NO: 2 and encompasses an epitope of CIP104 such that an antibody raised against the peptide forms a specific immune complex with CIP104. Preferably, the antigenic peptide comprises at least 10 amino acid residues, more preferably at least 15 amino acid residues, even more preferably at least 20 amino acid residues, and most preferably at least 30 amino acid residues. Preferred epitopes encompassed by the antigenic peptide are regions of CIP104 that are located on the surface of the protein, e.g., hydrophilic regions. A standard hydrophobicity analysis of the CIP104 protein sequence shown in SEQ ID NO: 2 can be performed to identify such hydrophilic regions.

A CIP104 immunogen typically is used to prepare antibodies by immunizing a suitable subject, (e.g., rabbit, goat, mouse or other mammal) with the immunogen. An appropriate immunogenic preparation can contain, for examples, recombinantly expressed CIP104 protein or a chemically synthesized CIP104 peptide. The preparation can further include an adjuvant, such as Freund's complete or incomplete adjuvant, or similar immunostimulatory agent. Immunization of a suitable subject with an immunogenic CIP104 preparation induces a polyclonal anti-CIP104 antibody response.

Accordingly, another aspect of the invention pertains to anti-CIP104 antibodies. Polyclonal anti-CIP104 antibodies can be prepared as described above by immunizing a suitable subject with a CIP104 immunogen. The anti-CIP104 antibody titer in the immunized subject can be monitored over time by standard techniques, such as with an enzyme linked immunosorbent assay (ELISA) using immobilized CIP104. If desired, the antibody molecules directed against CIP104 can be isolated from the mammal (e.g., from the blood) and further purified by well known techniques, such as protein A chromatography to obtain the IgG fraction. At an appropriate time after immunization, e.g., when the anti-CIP104 antibody titers are highest, antibody-producing cells can be obtained from the subject and used to prepare monoclonal antibodies by standard techniques, such as the hybridoma technique originally described by Kohler and Milstein (1975, *Nature* 256:495–497) (see also, Brown et al. (1981) *J. Immunol* 127:539–46; Brown et al. (1980) *J. Biol Chem* 255:4980–83; Yeh et al. (1976) *PNAS* 76:2927–31; and Yeh et al. (1982) *Int. J. Cancer* 29:269–75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77–96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387–402; M. L. Gefter et al. (1977) *Somatic Cell Genet.*, 3:231–36). Briefly, an immortal cell line (typically a myeloma) is fused to lymphocytes (typically splenocytes) from a mammal immunized with a CIP104 immunogen as described above, and the culture supernatants of the resulting hybridoma cells are screened to identify a hybridoma producing a monoclonal antibody that binds CIP104.

Any of the many well known protocols used for fusing lymphocytes and immortalized cell lines can be applied for the purpose of generating an anti-CIP104 monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinary skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines may be used as a fusion partner according to standard techniques, e.g., the P3-NS1/1-Ag4-1, P3-x63-Ag8.653 or Sp2/O-Ag14 myeloma lines. These myeloma lines are available from the American Type Culture Collection (ATCC), Rockville, Md. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind CIP104, e.g., using a standard ELISA assay.

Alternative to preparing monoclonal antibody-secreting hybridomas, a monoclonal anti-CIP104 antibody can be identified and isolated by screening a recombinant combinatorial immunoglobulin library (e.g., an antibody phage display library) with CIP104 to thereby isolate immunoglobulin library members that bind CIP104. Kits for generating and screening phage display libraries are commercially available (e.g., the Pharmacia *Recombinant Phage Antibody System*, Catalog No. 27-9400-01; and the Stratagene SurfZAP™ Phage Display Kit, Catalog No. 240612). Additionally, examples of methods and reagents particularly amenable for use in generating and screening antibody display library can be found in, for example, Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) *Bio/Technology*

9:1370–1372; Hay et al. (1992) *Hum Antibod Hybridomas* 3:81–85; Huse et al. (1989) *Science* 246:1275–1281; Griffiths et al. (1993) *EMBO J* 12:725–734; Hawkins et al. (1992) *J. Mol Biol* 226:889–896; Clarkson et al. (1991) *Nature* 352:624–628; Gram et al. (1992) *PNAS* 89:3576–3580; Garrad et al. (1991) *Bio/Technology* 9:1373–1377; Hoogenboom et al. (1991) *Nuc Acid Res* 19:4133–4137; Barbas et al. (1991) *PNAS* 88:7978–7982; and McCafferty et al. *Nature* (1990) 348:552–554.

Additionally, recombinant anti-CIP104 antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Patent Publication PCT/US86/02269; Akira, et al. European Patent Application 184,187; Taniguchi, M., European Patent Application 171,496; Morrison et al. European Patent Application 173,494; Neuberger et al. PCT Application WO 86/01533; Cabilly et al. U.S. Pat. No. 4,816,567; Cabilly et al. European Patent Application 125,023; Better et al. (1988) *Science* 240:1041–1043; Liu et al. (1987) *PNAS* 84:3439–3443; Liu et al. (1987) *J. Immunol.* 139:3521–3526; Sun et al. (1987) *PNAS* 84:214–218; Nishimura et al. (1987) *Canc. Res.* 47:999–1005; Wood et al. (1985) *Nature* 314:446–449; and Shaw et al. (1988) *J. Natl Cancer Inst.* 80:1553–1559); Morrison, S. L. (1985) *Science* 229:1202–1207; Oi et al. (1986) *BioTechniques* 4:214; Winter U.S. Pat. No. 5,225, 539; Jones et al. (1986) *Nature* 321:552–525; Verhoeyan et al. (1988) *Science* 239:1534; and Beidler et al. (1988) *J. Immunol.* 141:4053–4060.

An anti-CIP104 antibody (e.g., monoclonal antibody) can be used to isolate CIP104 by standard techniques, such as affinity chromatography or immunoprecipitation. An anti-CIP104 antibody can facilitate the purification of natural CIP104 from cells and of recombinantly produced CIP104 expressed in host cells. Moreover, an anti-CIP104 antibody can be used to detect CIP104 protein (e.g., in a cellular lysate or cell supernatant). Detection may be facilitated by coupling (i.e., physically linking) the antibody to a detectable substance. Accordingly, in one embodiment, an anti-CIP104 antibody of the invention is labeled with a detectable substance. Examples of detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^{125}I$, $^{131}I$, $^{35}S$ or $^3H$.

Yet another aspect of the invention pertains to anti-CIP104 antibodies that are obtainable by a process comprising:

(a) immunizing an animal with an immunogenic CIP104 protein, or an immunogenic portion thereof; and (b) isolating from the animal antibodies that specifically bind to a CIP104 protein. Methods for immunization and recovery of the specific anti-CIP104 antibodies are described further above.

V. Pharmaceutical Compositions

CIP104 modulators of the invention (e.g., CIP104 inhibitory or stimulatory agents, including CIP104 proteins and antibodies) can be incorporated into pharmaceutical compositions suitable for administration. Such compositions typically comprise the modulatory agent and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. For example, solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These may be prepared according to methods known to those skilled in the art, for example, as described in U.S. Pat. No. 4,522,811.

V. Methods of the Invention

Another aspect of the invention pertains to methods of using the various CIP104 compositions of the invention. For example, the invention provides a method for detecting the presence of CIP104 activity in a biological sample. The method involves contacting the biological sample with an agent capable of detecting CIP104 activity, such as CIP104 protein or CIP104 mRNA, such that the presence of CIP104 activity is detected in the biological sample.

A preferred agent for detecting CIP104 mRNA is a labeled nucleic acid probe capable of hybridizing to CIP104 mRNA. The nucleic acid probe can be, for example, the CIP104 cDNA of SEQ ID NO: 1, or a portion thereof, such as an oligonucleotide of at least 15, 30, 50, 100, 200, 300, 400, 500, 600, 700, 800, 900 or 1000 nucleotides in length and sufficient to specifically hybridize under stringent conditions to CIP104 mRNA.

A preferred agent for detecting CIP104 protein is a labeled antibody capable of binding to CIP104 protein. Antibodies can be polyclonal, or more preferably, monoclonal. An intact antibody, or a fragment thereof (e.g., Fab or F(ab')$_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids. For example, techniques for detection of CIP104 mRNA include Northern hybridizations and in situ hybridizations. Techniques for detection of CIP104 protein include enzyme linked immunosorbent assays (ELISAs), Western blots, immunoprecipitations and immunofluorescence.

The invention further provides methods for identifying compounds that modulate the activity of a CIP104 protein. For example, the invention provides a method for identifying a compound that modulates the activity of a CIP104 protein, comprising providing an indicator composition that comprises a CIP104 protein;

contacting the indicator composition with a test compound; and determining the effect of the test compound on the activity of the CIP104 protein in the indicator composition to thereby identify a compound that modulates the activity of a CIP104 protein.

In a preferred embodiment, the method identifies compounds that modulate the activity of CIP104 by modulating the interaction between CIP104 and CIITA. Accordingly, in a preferred embodiment of the above-described method, the indicator composition comprises a CIP104 protein and a CIITA protein and the effect of the test compound on the activity of the CIP104 protein is determined by determining the degree of interaction between the CIP104 protein and the CIITA protein the presence and absence of the test compound. The method can be carried out either in vitro or in vivo in cells. For example, for an in vitro assay, recombinant CIP104 and recombinant CIITA can be combined in the presence and absence of a test compound and the degree of interaction between CIP104 and CIITA in the presence and absence of the test compound can be determined by standard methods known in the art (e.g., by evaluating the amount of CIP104 co-precipitated with CIITA in the presence and absence of the test compound or by labeling one of the two proteins and evaluating the amount of labeled protein that associates with the nonlabeled protein in the presence and absence of the test compound). For an in vitro assay, CIP104 and CIITA can be expressed in a host cell that also contains a reporter gene whose expression is dependent upon interaction of CIP104 and CIITA. The effect of a test compound on the interaction between CIP104 and CIITA in the cell can then be evaluated by determining the level of expression of the reporter gene in the presence and absence of the test compound. For example, the two-hybrid assay used to isolate CIP104 (described further in Example 1) can be adapted to identifying test compounds that modulate the interaction of CIP104 with CIITA.

In another preferred embodiment, the method identifies compounds that modulate the activity of CIP104 by modulating the ability of CIP104 to enhance CIITA-regulated gene transcription. Accordingly, in another preferred embodiment of the above-described method, the indicator composition is a cell comprising a CIP104 protein, a CIITA protein and a reporter gene responsive to CIITA and the effect of the test compound on the activity of the CIP104 protein is determined by determining the level of expression of the reporter gene in the presence and absence of the test compound. Preferably, the reporter gene responsive to CIITA comprises a major histocompatibility complex (MHC) class II gene promoter. A preferred assay system for examining the effect of test compounds on CIP104 enhancement of CIITA-regulated gene expression is described further in Example 3, in which a host cell is transfected with (i) an expression vector encoding CIP104, (ii) an expression vector encoding CIITA and (ii) a DRα-CAT reporter gene construct. The level of CAT activity in the host cell in the presence and absence of a test compound can be used to determine the effect of the test compound on CIP 104-enhanced CIITA-regulated MHC class II gene expression.

The methods of the invention for identifying an agent that modulates CIP104 activity can further comprise determining the effect of the test compound on an immune response to thereby identify a compound that modulates an immune response.

Preferred methods of the invention for identifying agents that modulate the interaction between CIP104 and CIITA can comprise, for example,
a) combining:
  (i) CIP104, or an CIITA-interacting portion thereof; and
  (ii) an CIITA, or a CIP104-interacting portion thereof; in the presence and absence of a test compound;
b) determining the degree of interaction between (i) and (ii) in the presence and absence of the test compound; and
c) identifying an agent that modulates an interaction between CIP104 and CIITA.

Isolated CIP104 and/or CIITA may be used in the method, or, alternatively, only portions of CIP104 and/or CIITA may be used. For example, an isolated interaction domain of CIITA can be used as the CIP104-interacting portion of CIITA. Likewise, a portion of CIP104 capable of binding to the interaction domain of CIITA may be used. In a preferred embodiment, one or both of (i) and (ii) are fusion proteins, such as GST fusion proteins. The degree of interaction between (i) and (ii) can be determined, for example, by labeling one of the proteins with a detectable substance (e.g., a radiolabel), isolating the non-labeled protein and quantitating the amount of detectable substance that has become associated with the non-labeled protein. The assay can be used to identify agents that either stimulate or inhibit the interaction between CIP104 and CIITA. An agent that stimulates the interaction between CIP104 and CIITA is identified based upon its ability to increase the degree of interaction between (i) and (ii) as compared to the degree of interaction in the absence of the agent, whereas an agent that inhibits the interaction between CIP104 and CIITA is identified based upon its ability to decrease the degree of interaction between (i) and (ii) as compared to the degree of interaction in the absence of the agent. Assays systems for identifying agents that modulate SH2 domain-ligand interactions as described in U.S. Pat. No. 5,352,660 by Pawson can be adapted to identifying agents that modulate the CIP104/CIITA interactions.

Preferred methods of the invention for identifying a compound that modulates the expression or activity of CIP104 can comprise, for example,
a) preparing an indicator cell, wherein said indicator cell contains:
  i) a recombinant expression vector encoding CIP104; and
  ii) a vector comprising regulatory sequences of an MHC class II gene operatively linked a reporter gene;
b) contacting the indicator cell with a test compound;
c) determining the level of expression of the reporter gene in the indicator cell in the presence of the test compound;
d) comparing the level of expression of the reporter gene in the indicator cell in the presence of the test compound with the level of expression of the reporter gene in the indicator cell in the absence of the test compound; and
e) identifying a compound that modulates the expression or activity of CIP104.

Recombinant expression vectors that can be used for expression of CIP104 in an indicator cell are known in the art. In one embodiment, within the expression vector the CIP104 coding sequences are operatively linked to regulatory sequences that allow for constitutive expression of CIP104 in the indicator cell (e.g., viral regulatory sequences, such as a cytomegalovirus promoter/enhancer, can be used). Use of a recombinant expression vector that allows for constitutive expression of CIP104 in the indicator cell is preferred for identification of compounds that enhance or inhibit the activity of CIP104. In an alternative embodiment, within the expression vector the CIP104 coding sequences are operatively linked to regulatory sequences of the CIP104 gene (i.e., the promoter regulatory region derived from the endogenous CIP104 gene). Use of a recombinant expression vector in which CIP104 protein expression is controlled by the native regulatory sequences of the CIP104 gene is preferred for identification of compounds that enhance or inhibit the transcriptional expression of CIP104.

Preferably, the MHC class II regulatory sequences to which the reporter gene is linked are from a human MHC class II gene such as a DRα, DRβ, DQα, DQβ, DPα or DPβ gene, the promoter/enhancer sequences of which are well known in the art. In a particularly preferred embodiment, the reporter gene is linked to regulatory sequences of the DRa gene. Such a reporter gene construct is described further in Example 3.

A variety of reporter genes are known in the art and are suitable for use in the screening assays of the invention. Examples of suitable reporter genes include those which encode chloramphenicol acetyltransferase, beta-galactosidase, alkaline phosphatase or luciferase. Standard methods for measuring the activity of these gene products are known in the art. A variety of cell types are suitable for use as an indicator cell in the screening assay. Preferably a cell line is used which does not normally express CIP104 or expresses only low levels of endogenous CIP104.

In one embodiment, the level of expression of the reporter gene in the indicator cell in the presence of the test compound is higher than the level of expression of the reporter gene in the indicator cell in the absence of the test compound and the test compound is identified as a compound that stimulates the expression or activity of the transcription factor. In another embodiment, the level of expression of the reporter gene in the indicator cell in the presence of the test compound is lower than the level of expression of the reporter gene in the indicator cell in the absence of the test compound and the test compound is identified as a compound that inhibits the expression or activity of the transcription factor.

In yet another embodiment, the invention provides a method identifying a protein that interacts with CIP104 comprising:
a) providing a two hybrid assay including a host cell that contains:
  i) a reporter gene operably linked to a transcriptional regulatory sequence;

ii) a first chimeric gene that encodes a first fusion protein, said first fusion protein including CIP104;

iii) a library of second chimeric genes that encodes second fusion proteins;

wherein expression of the reporter gene is sensitive to interactions between the first fusion protein, the second fusion protein and the transcriptional regulatory sequence;

b) determining the level of expression of the reporter gene in the host cell; and c) identifying a protein that interacts with CIP104.

The method of the invention for identifying proteins that interact with CIP104 can be designed based on the two-hybrid assay system (also referred to as an interaction trap assay) known in the art (see e.g., Field U.S. Pat. No. 5,283,173; Zervos et al. (1993) *Cell* 72:223–232; Madura et al. (1993) *J. Biol. Chem.* 268:12046–12054; Bartel et al. (1993) *Biotechniques* 14:920–924; and Iwabuchi et al. (1993) *Oncogene* 8:1693–1696). The two-hybrid assay is generally used for identifying proteins that interact with a particular target protein. The assay employs gene fusions to identify proteins capable of interacting to reconstitute a functional transcriptional activator. The transcriptional activator consists of a DNA-binding domain and a transcriptional activation domain, wherein both domains are required to activate transcription of genes downstream from a target sequence (such as an upstream activator sequence (UAS) for GAL4). DNA sequences encoding a target "bait" protein are fused to either of these domains and a library of DNA sequences is fused to the other domain. "Fish" fusion proteins (generated from the fusion library) capable of binding to the target-fusion protein (e.g., a target GAL4-fusion "bait") will generally bring the two domains (DNA-binding domain and transcriptional activation domain) into close enough proximity to activate the transcription of a reporter gene inserted downstream from the target sequence. Thus, the "fish" proteins can be identified by their ability to reconstitute a functional transcriptional activator (e.g., a functional GAL4 transactivator).

This general two-hybrid system can be applied to the identification of proteins that interact with CIP104 by construction of a target CIP104 fusion protein (e.g., a CIP104/GAL4 binding domain fusion as the "bait") and a cDNA library of "fish" fusion proteins (e.g., a cDNA/GAL4 activation domain library). The cDNA library can be prepared from a cell type of interest to identify proteins in that cell type that interact with CIP104. The expression vector encoding the CIP104 fusion protein and the cDNA library are then introduced into a host cell that also contains a reporter gene construct linked to a regulatory sequence to which the "bait" fusion protein binds (such as an upstream activator sequence (UAS) for GAL4). cDNAs encoding proteins that interact with CIP104 can be identified based upon transactivation of the reporter gene construct.

Yet another aspect of the invention pertains to methods of modulating CIP104 activity in a cell. The modulatory methods of the invention involve contacting the cell with an agent that modulates CIP104 activity such that CIP104 activity in the cell is modulated. The agent may act by modulating the activity of CIP104 protein in the cell or by modulating transcription of the CIP104 gene or translation of the CIP104 mRNA. As used herein, the term "modulating" is intended to include inhibiting or decreasing CIP104 activity and stimulating or increasing CIP104 activity. Accordingly, in one embodiment, the agent inhibits CIP104 activity. An inhibitory agent may function, for example, by directly inhibiting CIP104 activity or by inhibiting an interaction between CIP104 and CIITA. In another embodiment, the agent stimulates CIP104 activity. A stimulatory agent may function, for example, by directly stimulating CIP104 activity or by promoting an interaction between CIP104 and CIITA.

A. Inhibitory Agents

According to a modulatory method of the invention, CIP104 activity is inhibited in a cell by contacting the cell with an inhibitory agent. Inhibitory agents of the invention can be, for example, intracellular binding molecules that act to inhibit the expression or activity of CIP104. As used herein, the term "intracellular binding molecule" is intended to include molecules that act intracellularly to inhibit the expression or activity of a protein by binding to the protein itself, to a nucleic acid (e.g., an mRNA molecule) that encodes the protein or to a second protein with which the first protein normally interacts (e.g., molecules that bind to CIITA to thereby inhibit the interaction between CIP104 and CIITA). Examples of intracellular binding molecules, described in further detail below, include antisense CIP104 nucleic acid molecules (e.g., to inhibit translation of CIP104 mRNA), intracellular anti-CIP104 antibodies (e.g., to inhibit the activity of CIP104 protein) and dominant negative mutants of the CIP104 protein.

In one embodiment, an inhibitory agent of the invention is an antisense nucleic acid molecule that is complementary to a gene encoding CIP104, or to a portion of said gene, or a recombinant expression vector encoding said antisense nucleic acid molecule. The use of antisense nucleic acids to downregulate the expression of a particular protein in a cell is well known in the art (see e.g., Weintraub, H. et al., Antisense RNA as a molecular tool for genetic analysis, *Reviews—Trends in Genetics, Vol.* 1(1) 1986; Askari, F. K. and McDonnell, W. M. (1996) *N. Eng. J. Med.* 334:316–318; Bennett, M. R. and Schwartz, S. M. (1995) *Circulation* 92:1981–1993; Mercola, D. and Cohen, J. S. (1995) *Cancer Gene Ther.* 2:47–59; Rossi, J. J. (1995) *Br. Med. Bull.* 51:217–225; Wagner, R. W. (1994) *Nature* 372:333–335). An antisense nucleic acid molecule comprises a nucleotide sequence that is complementary to the coding strand of another nucleic acid molecule (e.g., an mRNA sequence) and accordingly is capable of hydrogen bonding to the coding strand of the other nucleic acid molecule. Antisense sequences complementary to a sequence of an mRNA can be complementary to a sequence found in the coding region of the mRNA, the 5' or 3' untranslated region of the mRNA or a region bridging the coding region and an untranslated region (e.g., at the junction of the 5' untranslated region and the coding region). Furthermore, an antisense nucleic acid can be complementary in sequence to a regulatory region of the gene encoding the mRNA, for instance a transcription initiation sequence or regulatory element. Preferably, an antisense nucleic acid is designed so as to be complementary to a region preceding or spanning the initiation codon on the coding strand or in the 3' untranslated region of an mRNA. An antisense nucleic acid for inhibiting the expression of CIP104 protein in a cell can be designed based upon the nucleotide sequence encoding the CIP104 protein (e.g., SEQ ID NO: 1, or a portion thereof), constructed according to the rules of Watson and Crick base pairing.

An antisense nucleic acid can exist in a variety of different forms. For example, the antisense nucleic acid can be an oligonucleotide that is complementary to only a portion of a CIP104 gene. An antisense oligonucleotides can be constructed using chemical synthesis procedures known in the art. An antisense oligonucleotide can be chemically synthesized using naturally occurring nucleotides or variously modified nucleotides designed to increase the biological stability of the molecules or to increase the physical stability of the duplex formed between the antisense and sense nucleic acids, e.g. phosphorothioate derivatives and acridine substituted nucleotides can be used. To inhibit CIP104 expression in cells in culture, one or more antisense oligonucleotides can be added to cells in culture media, typically at about 200 µg oligonucleotide/ml.

Alternatively, an antisense nucleic acid can be produced biologically using an expression vector into which a nucleic acid has been subcloned in an antisense orientation (i.e., nucleic acid transcribed from the inserted nucleic acid will be of an antisense orientation to a target nucleic acid of interest). Regulatory sequences operatively linked to a nucleic acid cloned in the antisense orientation can be chosen which direct the expression of the antisense RNA molecule in a cell of interest, for instance promoters and/or enhancers or other regulatory sequences can be chosen which direct constitutive, tissue specific or inducible expression of antisense RNA. For example, for inducible expression of antisense RNA, an inducible eukaryotic regulatory system, such as the Tet system (e.g., as described in Gossen, M. and Bujard, H. (1992) *Proc. Natl. Acad. Sci.* USA 89:5547–5551; Gossen, M. et al. (1995) *Science* 268:1766–1769; PCT Publication No. WO 94/29442; and PCT Publication No. WO 96/01313) can be used. The antisense expression vector is prepared as described above for recombinant expression vectors, except that the cDNA (or portion thereof) is cloned into the vector in the antisense orientation. The antisense expression vector can be in the form of, for example, a recombinant plasmid, phagemid or attenuated virus. The antisense expression vector is introduced into cells using a standard transfection technique, as described above for recombinant expression vectors.

In another embodiment, an antisense nucleic acid for use as an inhibitory agent is a ribozyme. Ribozymes are catalytic RNA molecules with ribonuclease activity which are capable of cleaving a single-stranded nucleic acid, such as an mRNA, to which they have a complementary region (for reviews on ribozymes see e.g., Ohkawa, J. et al. (1995) *J. Biochem.* 118:251–258; Sigurdsson, S. T. and Eckstein, F. (1995) *Trends Biotechnol.* 13:286–289; Rossi, J. J. (1995) *Trends Biotechnol.* 13:301–306; Kiehntopf, M. et al. (1995) *J. Mol. Med.* 73:65–71). A ribozyme having specificity for CIP104 mRNA can be designed based upon the nucleotide sequence of the CIP104 cDNA. For example, a derivative of a Tetrahymena L-19 IVS RNA can be constructed in which the base sequence of the active site is complementary to the base sequence to be cleaved in a CIP104 mRNA. See for example U.S. Pat. Nos. 4,987,071 and 5,116,742, both by Cech et al. Alternatively, CIP104 mRNA can be used to select a catalytic RNA having a specific ribonuclease activity from a pool of RNA molecules. See for example Bartel, D. and Szostak, J. W. (1993) *Science* 261: 1411–1418.

Another type of inhibitory agent that can be used to inhibit the expression and/or activity of CIP104 in a cell is an intracellular antibody specific for the CIP104 protein. The use of intracellular antibodies to inhibit protein function in a cell is known in the art (see e.g., Carlson, J. R. (1988) *Mol. Cell. Biol.* 8:2638–2646; Biocca, S. et al. (1990) *EMBO J.* 9:101–108; Werge, T. M. et al. (1990) *FEBS Letters* 274:193–198; Carlson, J. R. (1993) *Proc. Natl. Acad. Sci. USA* 90:7427–7428; Marasco, W. A. et al. (1993) *Proc. Natl. Acad. Sci.* USA 90:7889–7893; Biocca, S. et al. (1994) *Bio/Technology* 12:396–399; Chen, S-Y. et al. (1994) *Human Gene Therapy* 5:595–601; Duan, L et al. (1994) *Proc. Natl. Acad. Sci. USA* 91:5075–5079; Chen, S-Y. et al. (1994) *Proc. Natl. Acad. Sci.* USA 91:5932–5936; Beerli, R. R. et al. (1994) *J. Biol. Chem.* 269:23931–23936; Beerli, R. R. et al. (1994) *Biochem. Biophys. Res. Commun.* 204:666–672; Mhashilkar, A. M. et al. (1995) *EMBO J.* 14:1542–1551; Richardson, J. H. et al. (1995) *Proc. Natl. Acad. Sci. USA* 92:3137–3141; PCT Publication No. WO 94/02610 by Marasco et al.; and PCT Publication No. WO 95/03832 by Duan et al.).

To inhibit protein activity using an intracellular antibody, a recombinant expression vector is prepared which encodes the antibody chains in a form such that, upon introduction of the vector into a cell, the antibody chains are expressed as a functional antibody in an intracellular compartment of the cell. For inhibition of CIP104 activity according to the inhibitory methods of the invention, an intracellular antibody that specifically binds the CIP104 protein is expressed in the cytoplasm of the cell. To prepare an intracellular antibody expression vector, antibody light and heavy chain cDNAs encoding antibody chains specific for the target protein of interest, e.g., CIP104, are isolated, typically from a hybridoma that secretes a monoclonal antibody specific for the CIP104 protein. Hybridomas secreting anti-CIP104 monoclonal antibodies, or recombinant anti-CIP104 monoclonal antibodies, can be prepared as described above. Once a monoclonal antibody specific for CIP104 protein has been identified (e.g., either a hybridoma-derived monoclonal antibody or a recombinant antibody from a combinatorial library), DNAs encoding the light and heavy chains of the monoclonal antibody are isolated by standard molecular biology techniques. For hybridoma derived antibodies, light and heavy chain cDNAs can be obtained, for example, by PCR amplification or eDNA library screening. For recombinant antibodies, such as from a phage display library, cDNA encoding the light and heavy chains can be recovered from the display package (e.g., phage) isolated during the library screening process. Nucleotide sequences of antibody light and heavy chain genes from which PCR primers or cDNA library probes can be prepared are known in the art. For example, many such sequences are disclosed in Kabat, E. A., et al. (1991) *Sequences of Proteins of Immunological Interest, Fifth Edition*, U.S. Department of Health and Human Services, NIH Publication No. 91-3242 and in the "Vbase" human germline sequence database.

Once obtained, the antibody light and heavy chain sequences are cloned into a recombinant expression vector using standard methods. To allow for cytoplasmic expression of the light and heavy chains, the nucleotide sequences encoding the hydrophobic leaders of the light and heavy chains are removed. An intracellular antibody expression vector can encode an intracellular antibody in one of several different forms. For example, in one embodiment, the vector encodes full-length antibody light and heavy chains such that a full-length antibody is expressed intracellularly. In another embodiment, the vector encodes a full-length light chain but only the VH/CH1 region of the heavy chain such that a Fab fragment is expressed intracellularly. In the most preferred embodiment, the vector encodes a single chain antibody (scFv) wherein the variable regions of the light and heavy chains are linked by a flexible peptide linker (e.g., $(Gly_4Ser)_3$) and expressed as a single chain molecule. To inhibit CIP104 activity in a cell, the expression vector encoding the anti-CIP104 intracellular antibody is introduced into the cell by standard transfection methods, as discussed hereinbefore.

Other inhibitory agents that can be used to inhibit the activity of a CIP104 protein are chemical compounds that, directly inhibit CIP104 activity or inhibit the interaction between CIP104 and CIITA. Such compounds can be identified using screening assays that select for such compounds, as described in detail above.

Yet another form of an inhibitory agent of the invention is an inhibitory form of a CIP104 protein, also referred to herein as a dominant negative inhibitor. A dominant negative inhibitor can be a form of a CIP104 protein that retains the ability to interact with CIITA but that lacks one or more other functional activities such that the dominant negative form of CIP104 acts to inhibit the ability of the CIP1 04/CIITA complex to activate transcription. This dominant negative form of a CIP104 protein may be, for example, a mutated form of CIP104 in which the region of the protein that interacts with CIITA is conserved but in which one or more amino acid residues elsewhere in the protein are mutated. Such dominant negative CIP104 proteins can be expressed in cells using a recombinant expression vector encoding the mutant CIP104 protein, which is introduced into the cell by standard transfection methods. Mutation or deletion of specific codons within the CIP104-encoding cDNA can be performed using standard mutagenesis methods. The mutated cDNA is inserted into a recombinant expression vector, which is then introduced into a cell to allow for expression of the mutated CIP104 protein. The ability of the mutant CIP104 protein to interact with CIITA can be assessed using standard in vitro interaction assays. The effect of the mutant CIP104 protein on transcriptional activation can be assessed, for example, by expressing the mutant CIP104 protein in indicator cells in culture, together with a reporter gene comprising an MHC class II promoter, and assessing the effect of the mutant CIP104 protein in transcription of the reporter gene. The indicator cells should express endogenous CIITA or should be transfected to express CIITA. A mutant form of CIP104 that retains the ability to interact with CIP104 but that interferes with transcriptional activation from MHC class II promoters when co-expressed in cells with CIITA can be selected as a dominant negative inhibitor of CIP104 activity.

Other inhibitory agents that can be used to inhibit the activity of a CIP104 protein are chemical compounds that inhibit the interaction between CIP104 and CIITA. Such compounds can be identified using screening assays that select for such compounds, as described in detail above.

B. Stimulatory Agents

According to a modulatory method of the invention, CIP104 activity is stimulated in a cell by contacting the cell with a stimulatory agent. Examples of such stimulatory agents include active CIP104 protein and nucleic acid molecules encoding CIP104 that are introduced into the cell to increase CIP104 activity in the cell. A preferred stimulatory agent is a nucleic acid molecule encoding a CIP104 protein, wherein the nucleic acid molecule is introduced into the cell in a form suitable for expression of the active CIP104 protein in the cell. To express a CIP104 protein in a cell, typically a CIP104 cDNA is first introduced into a recombinant expression vector using standard molecular biology techniques, as described herein. A CIP104 cDNA can be obtained, for example, by amplification using the polymerase chain reaction (PCR) or by screening an appropriate cDNA library as described herein. Following isolation or amplification of CIP104 cDNA, the DNA fragment is introduced into an expression vector and transfected into target cells by standard methods, as described herein.

Other stimulatory agents that can be used to stimulate the activity of a CIP104 protein are chemical compounds that stimulate CIP104 activity in cells, such as compounds that directly stimulate CIP104 protein and compounds that promote the interaction between CIP104 and CIITA. Such compounds can be identified using screening assays that select for such compounds, as described in detail above.

The modulatory methods of the invention can be performed in vitro (e.g., by culturing the cell with the agent or by introducing the agent into cells in culture) or, alternatively, in vivo (e.g., by administering the agent to a subject or by introducing the agent into cells of a subject, such as by gene therapy). For practicing the modulatory method in vitro, cells can be obtained from a subject by standard methods and incubated (i.e., cultured) in vitro with a modulatory agent of the invention to modulate CIP104 activity in the cells. For example, peripheral blood mononuclear cells (PBMCs) can be obtained from a subject and isolated by density gradient centrifugation, e.g., with Ficoll/Hypaque. Specific cell populations can be depleted or enriched using standard methods. For example, monocytes/macrophages can be isolated by adherence on plastic. B cells, which normally constitutively express MHC class II molecules, can be enriched for example, by positive selection using antibodies to B cell surface markers, for example by incubating cells with a specific primary monoclonal antibody (mAb), followed by isolation of cells that bind the mAb using magnetic beads coated with a secondary antibody that binds the primary mAb. Specific cell populations (e.g., B cells) can also be isolated by fluorescence activated cell sorting according to standard methods. Monoclonal antibodies to B cell-specific surface markers known in the art and many are commercially available. If desired, cells treated in vitro with a modulatory agent of the invention can be readministered to the subject. For administration to a subject, it may be preferable to first remove residual agents in the culture from the cells before administering them to the subject. This can be done for example by a Ficoll/Hypaque gradient centrifugation of the cells. For further discussion of ex vivo genetic modification of cells followed by readministration to a subject, see also U.S. Pat. No. 5,399,346 by W. F. Anderson et al.

For practicing the modulatory method in vivo in a subject, the modulatory agent can be administered to the subject such that CIP104 activity in cells of the subject is modulated. The term "subject" is intended to include living organisms in which an immune response can be elicited. Preferred subjects are mammals. Examples of subjects include humans, monkeys, dogs, cats, mice, rats, cows, horses, goats and sheep.

For stimulatory or inhibitory agents that comprise nucleic acids (including recombinant expression vectors encoding CIP104 protein, antisense RNA, intracellular antibodies or dominant negative inhibitors), the agents can be introduced into cells of the subject using methods known in the art for introducing nucleic acid (e.g., DNA) into cells in vivo. Examples of such methods encompass both non-viral and viral methods, including:

Direct Injection: Naked DNA can be introduced into cells in vivo by directly injecting the DNA into the cells (see e.g., Acsadi et al. (1991) *Nature* 332:815–818; Wolff et al. (1990) *Science* 247:1465–1468). For example, a delivery apparatus (e.g., a "gene gun") for injecting DNA into cells in vivo can be used. Such an apparatus is commercially available (e.g., from BioRad).

Cationic Lipids: Naked DNA can be introduced into cells in vivo by complexing the DNA with cationic lipids or encapsulating the DNA in cationic liposomes. Examples of suitable cationic lipid formulations include N-[-1-(2,3-dioleoyloxy)propyl]N,N,N-triethylammonium chloride (DOTMA) and a 1:1 molar ratio of 1,2-dimyristyloxypropyl-3-dimethylhydroxyethylammonium bromide (DMRIE) and dioleoyl phosphatidylethanolamine (DOPE) (see e.g., Logan, J. J. et al. (1995) *Gene Therapy* 2:38–49; San, H. et al. (1993) *Human Gene Therapy* 4:781–788).

Receptor-Mediated DNA Uptake: Naked DNA can also be introduced into cells in vivo by complexing the DNA to a cation, such as polylysine, which is coupled to a ligand for a cell-surface receptor (see for example Wu, G. and Wu, C. H. (1988) *J. Biol. Chem.* 263:14621; Wilson et al. (1992) *J. Biol. Chem.* 267:963–967; and U.S. Pat. No. 5,166,320). Binding of the DNA-ligand complex to the receptor facilitates uptake of the DNA by receptor-mediated endocytosis. A DNA-ligand complex linked to adenovirus capsids which naturally disrupt endosomes, thereby releasing material into the cytoplasm can be used to avoid degradation of the complex by intracellular lysosomes (see for example Curiel et al. (1991) *Proc. Natl. Acad. Sci.* USA 88:8850; Cristiano et al. (1993) *Proc. Natl. Acad. Sci.* USA 90:2122–2126).

Retroviruses: Defective retroviruses are well characterized for use in gene transfer for gene therapy purposes (for a review see Miller, A. D. (1990) *Blood* 76:271). A recombinant retrovirus can be constructed having a nucleotide sequences of interest incorporated into the retroviral genome. Additionally, portions of the retroviral genome can be removed to render the retrovirus replication defective. The replication defective retrovirus is then packaged into virions which can be used to infect a target cell through the use of a helper virus by standard techniques. Protocols for producing recombinant retroviruses and for infecting cells in vitro or in vivo with such viruses can be found in *Current Protocols in Molecular Biology*, Ausubel, F. M. et al. (eds.) Greene Publishing Associates, (1989), Sections 9.10–9.14 and other standard laboratory manuals. Examples of suitable retroviruses include pLJ, pZIP, pWE and pEM which are well known to those skilled in the art. Examples of suitable packaging virus lines include ψCrip, ψCre, ψ2 and ψAm. Retroviruses have been used to introduce a variety of genes into many different cell types, including epithelial cells, endothelial cells, lymphocytes, myoblasts, hepatocytes, bone marrow cells, in vitro and/or in vivo (see for example Eglitis, et al. (1985) *Science* 230:1395–1398; Danos and Mulligan (1988) *Proc. Natl. Acad. Sci.* USA 85:6460–6464; Wilson et al. (1988) *Proc. Natl. Acad. Sci.* USA 85:3014–3018; Armentano et al. (1990) *Proc. Natl. Acad. Sci.* USA 87:6141–6145; Huber et al. (1991) *Proc. Natl. Acad. Sci. USA* 88:8039–8043; Ferry et al. (1991) *Proc. Natl. Acad. Sci.* USA 88:8377–8381; Chowdhury et al. (1991) *Science* 254:1802–1805; van Beusechem et al. (1992) *Proc. Natl. Acad. Sci.* USA 89:7640–7644; Kay et al. (1992) *Human Gene Therapy* 3:641–647; Dai et al. (1992) *Proc. Natl. Acad. Sci.* USA 89:10892–10895; Hwu et al. (1993) *J. Immunol.* 150:4104–4115; U.S. Pat. No. 4,868,116; U.S. Pat. No. 4,980,286; PCT Application WO 89/07136; PCT Application WO 89/02468; PCT Application WO 89/05345; and PCT Application WO 92/07573). Retroviral vectors require target cell division in order for the retroviral genome (and foreign nucleic acid inserted into it) to be integrated into the host genome to stably introduce nucleic acid into the cell. Thus, it may be necessary to stimulate replication of the target cell.

Adenoviruses: The genome of an adenovirus can be manipulated such that it encodes and expresses a gene product of interest but is inactivated in terms of its ability to replicate in a normal lytic viral life cycle. See for example Berkner et al. (1988) *BioTechniques* 6:616 Rosenfeld et al. (1991) *Science* 252:431–434; and Rosenfeld et al. (1992) *Cell* 68:143–155. Suitable adenoviral vectors derived from the adenovirus strain Ad type 5 d1324 or other strains of adenovirus (e.g., Ad2, Ad3, Ad7 etc.) are well known to those skilled in the art. Recombinant adenoviruses are advantageous in that they do not require dividing cells to be effective gene delivery vehicles and can be used to infect a wide variety of cell types, including airway epithelium (Rosenfeld et al. (1992) cited supra), endothelial cells (Lemarchand et al. (1992) *Proc. Natl. Acad. Sci.* USA 89:6482–6486), hepatocytes (Herz and Gerard (1993) *Proc. Natl. Acad. Sci.* USA 90:2812–2816) and muscle cells (Quantin et al. (1992) *Proc. Natl. Acad. Sci.* USA 89:2581–2584). Additionally, introduced adenoviral DNA (and foreign DNA contained therein) is not integrated into the genome of a host cell but remains episomal, thereby avoiding potential problems that can occur as a result of insertional mutagenesis in situations where introduced DNA becomes integrated into the host genome (e.g., retroviral DNA). Moreover, the carrying capacity of the adenoviral genome for foreign DNA is large (up to 8 kilobases) relative to other gene delivery vectors (Berkner et al. cited supra; Haj-Ahmand and Graham (1986) *J. Virol.* 57:267). Most replication-defective adenoviral vectors currently in use are deleted for all or parts of the viral E1 and E3 genes but retain as much as 80% of the adenoviral genetic material.

Adeno-Associated Viruses: Adeno-associated virus (AAV) is a naturally occurring defective virus that requires another virus, such as an adenovirus or a herpes virus, as a helper virus for efficient replication and a productive life cycle. (For a review see Muzyczka et al. *Curr. Topics in Micro. and Immunol*, (1992) 158:97–129). It is also one of the few viruses that may integrate its DNA into non-dividing cells, and exhibits a high frequency of stable integration (see for example Flotte et al. (1992) *Am. J Respir. Cell. Mol. Biol.* 7:349–356; Samulski et al. (1989) *J. Virol.* 63:3822–3828; and McLaughlin et al. (1989) *J. Virol.* 62:1963–1973). Vectors containing as little as 300 base pairs of AAV can be packaged and can integrate. Space for exogenous DNA is limited to about 4.5 kb. An AAV vector such as that described in Tratschin et al. (1985) *Mol. Cell. Biol.* 5:3251–3260 can be used to introduce DNA into cells. A variety of nucleic acids have been introduced into different cell types using AAV vectors (see for example Hermonat et al. (1984) *Proc. Natl. Acad. Sci. USA* 81:6466–6470; Tratschin et al. (1985) *Mol. Cell. Biol.* 4:2072–2081; Wondisford et al. (1988) *Mol. Endocrinol.* 2:32–39; Tratschin et al. (1984) *J. Virol.* 51:611–619; and Flotte et al. (1993) *J. Biol. Chem.* 268:3781–3790).

The efficacy of a particular expression vector system and method of introducing nucleic acid into a cell can be assessed by standard approaches routinely used in the art. For example, DNA introduced into a cell can be detected by a filter hybridization technique (e.g., Southern blotting) and RNA produced by transcription of introduced DNA can be detected, for example, by Northern blotting, RNase protection or reverse transcriptase-polymerase chain reaction (RT-PCR). The gene product can be detected by an appropriate assay, for example by immunological detection of a produced protein, such as with a specific antibody, or by a functional assay to detect a functional activity of the gene product.

A modulatory agent, such as a chemical compound that modulates the CIP104/CIITA interaction, can be administered to a subject as a pharmaceutical composition. Such compositions typically comprise the modulatory agent and a pharmaceutically acceptable carrier. As used herein the term "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Pharmaceutical compositions can be prepared as described above in subsection IV.

Modulation of CIP104 activity may be beneficial in a variety of clinical situations in which is desirable to modulate MHC class II gene expression, e.g., to thereby modulate an immune response, as discussed further below Immunodeficiencies: Upregulation of MHC class II gene expression through the use of an agent that modulates CIP104 activity may be beneficial in a variety of clinical disorders characterized by general or specific immunodeficiency, in particular in congenital immunodeficiency diseases characterized by defective MHC class II gene expression. In a preferred embodiment, MHC class II deficiency syndrome caused by a mutation in CIITA is treated by providing a normal CIITA to the patients (e.g., by gene therapy with a CIITA gene) in combination with upregulating CIP104 activity (e.g., by gene therapy with a CIP104 gene).

Infectious Diseases: Upregulation of MHC class II gene expression through the use of an agent that modulates CIP104 activity may be beneficial in a variety of infectious disease, as a means to promote an immune response against the infectious agent through more effective antigen presentation. Such infectious diseases include bacterial, viral, fungal and parasitic infections.

Cancer: Upregulation of MHC class II gene expression through the use of an agent that modulates CIP104 activity may be beneficial in a variety of malignancies, as a means to promote an immune response against the malignancy through more effective antigen presentation.

Autoimmune Diseases: Downregulation of MHC class II gene expression through the use of an agent that modulates CIP104 activity may be beneficial in a variety of autoimmune diseases, as a means to downregulate an immune response against autoantigens by inhibiting MHC-mediated presentation of the autoantigens. It is known in the art that autoimmune disorders can result from inappropriate expression of MHC class II genes on cells that do not normally express MHC class II genes, leading to aberrant presentation of autoantigens. Non-limiting examples of autoimmune diseases and disorders having an autoimmune component that may be treated according to the modulatory methods of the invention include diabetes mellitus, arthritis (including rheumatoid arthritis, juvenile rheumatoid arthritis, osteoarthritis, psoriatic arthritis), multiple sclerosis, myasthenia gravis, systemic lupus erythematosis, autoimmune thyroiditis, dermatitis (including atopic dermatitis and eczematous dermatitis), psoriasis, Sjögren's Syndrome, including keratoconjunctivitis sicca secondary to Sjögren's Syndrome, alopecia areata, allergic responses due to arthropod bite reactions, Crohn's disease, aphthous ulcer, iritis, conjunctivitis, keratoconjunctivitis, ulcerative colitis, asthma, allergic asthma, cutaneous lupus erythematosus, scleroderma, vaginitis, proctitis, drug eruptions, leprosy reversal reactions, erythema nodosum leprosum, autoimmune uveitis, allergic encephalomyelitis, acute necrotizing hemorrhagic encephalopathy, idiopathic bilateral progressive sensorineural hearing loss, aplastic anemia, pure red cell anemia, idiopathic thrombocytopenia, polychondritis, Wegener's granulomatosis, chronic active hepatitis, Stevens-Johnson syndrome, idiopathic sprue, lichen planus, Crohn's disease, Graves ophthalmopathy, sarcoidosis, primary biliary cirrhosis, uveitis posterior, and interstitial lung fibrosis.

The efficacy of a modulatory agent in ameliorating autoimmune diseases can be tested in an animal models of human diseases. Such animal models include experimental allergic encephalomyelitis as a model of multiple sclerosis, the NOD mice as a model for diabetes, the mrl/lpr/lpr mouse as a model for lupus erythematosus, murine collagen-induced arthritis as a model for rheumatoid aritis, and murine experimental myasthenia gravis (see Paul ed., *Fundamental Immunology*, Raven Press, New York, 1989, pp. 840–856). A modulatory (i.e., stimulatory or inhibitory) agent of the invention is administered to test animals and the course of the disease in the test animals is then monitored by the standard methods for the particular model being used. Effectiveness of the modulatory agent is evidenced by amelioration of the disease condition in animals treated with the agent as compared to untreated animals (or animals treated with a control agent).

Transplantation: Downregulation of MHC class II gene expression through the use of an agent that modulates CIP104 activity may be beneficial in transplantation, as a means to downregulate an immune response against an allograft or to inhibit graft-versus-host disease. Accordingly, the modulatory methods of the invention can be used both in solid organ transplantation and in bone marrow transplantation.

This invention is further illustrated by the following examples which should not be construed as limiting. The contents of all references, patents and published patent applications cited throughout this application are hereby incorporated by reference. Nucleotide and amino acid sequences deposited in public databases as referred to herein are also hereby incorporated by reference.

EXAMPLE 1

Isolation of a CIP104 cDNA Using a Yeast Two-Hybrid Interaction Trap Assay

A yeast two-hybrid interaction trap assay was used to isolate proteins that could directly bind to the MHC-transactivator protein CIITA. A CIITA-Gal4 fusion protein was prepared for use as the "bait" in the yeast two-hybrid assay by cloning a fragment of human CIITA that had an internal deletion of amino acid residues 21 to 134 (referred to herein as CIITA.ΔAD) into the vector pEG202 (Gyuris, J. et al. (1993) *Cell* 75:791–803) to thereby create an in-frame CIITA.ΔAD-Gal4 fusion. The CIITA.ΔAD fragment lacks the transcriptional activation domain of CIITA (at about residues 21–134) but retains a proline-serine-threonine (P-S-T) rich region at about residues 135–292. This bait was used to screen a cDNA library prepared from a human Raji cDNA library to select for clones encoding polypeptides that interacted with the bait, using methodologies known in the art (see e.g., Gyuris, J. et al. (1993) *Cell* 75:791–803).

A partial cDNA of approximately 1.4 kb was isolated using the two-hybrid assay and this partial cDNA was used as a probe to isolate an approximately 4.2 kb cDNA using standard hybridization methods. The nucleotide and predicted amino acid sequences of the isolated 4.2 kb cDNA are shown in SEQ ID NOs: 1 and 2, respectively. The coding region of SEQ ID NO: 1 extends from nucleotides 509 to 3343, encoding a protein of 945 amino acids having a predicted molecular weight of approximately 104 kD. The encoded protein was termed CIITA-Interacting Protein 104 (CIP104). Additional characterization demonstrated that CIP104 was able to interact with a CIITA in which the activation domain had been removed (i.e., the CIITA.ΔAD fragment used to isolate CIP104) but was unable to interact with a fragment of CIITA in which both the activation domain and the P-S-T region had been removed. Accordingly, these experiments demonstrate that the P-S-T region of CIITA is necessary for binding to CIP104.

EXAMPLE 2

Tissue Expression of CIP104 mRNA

To analyze the expression pattern of CIP104 mRNA, a multi-tissue Northern blot was probed with a CIP104 specific probe using standard Northern hybridization methods. The results are shown in FIG. 1. CIP104 mRNA was found to be expressed in most tissues examined, including heart, placenta, lung, liver, skeletal muscle, kidney, pancreas, spleen, thymus, prostate, testis, small intestine, colon and peripheral blood lymphocytes (PBL). The highest level of expression of CIP104 mRNA was observed in thymus.

EXAMPLE 3

Functional Activity of CIP104 in Regulating Gene Expression

Figure 2:
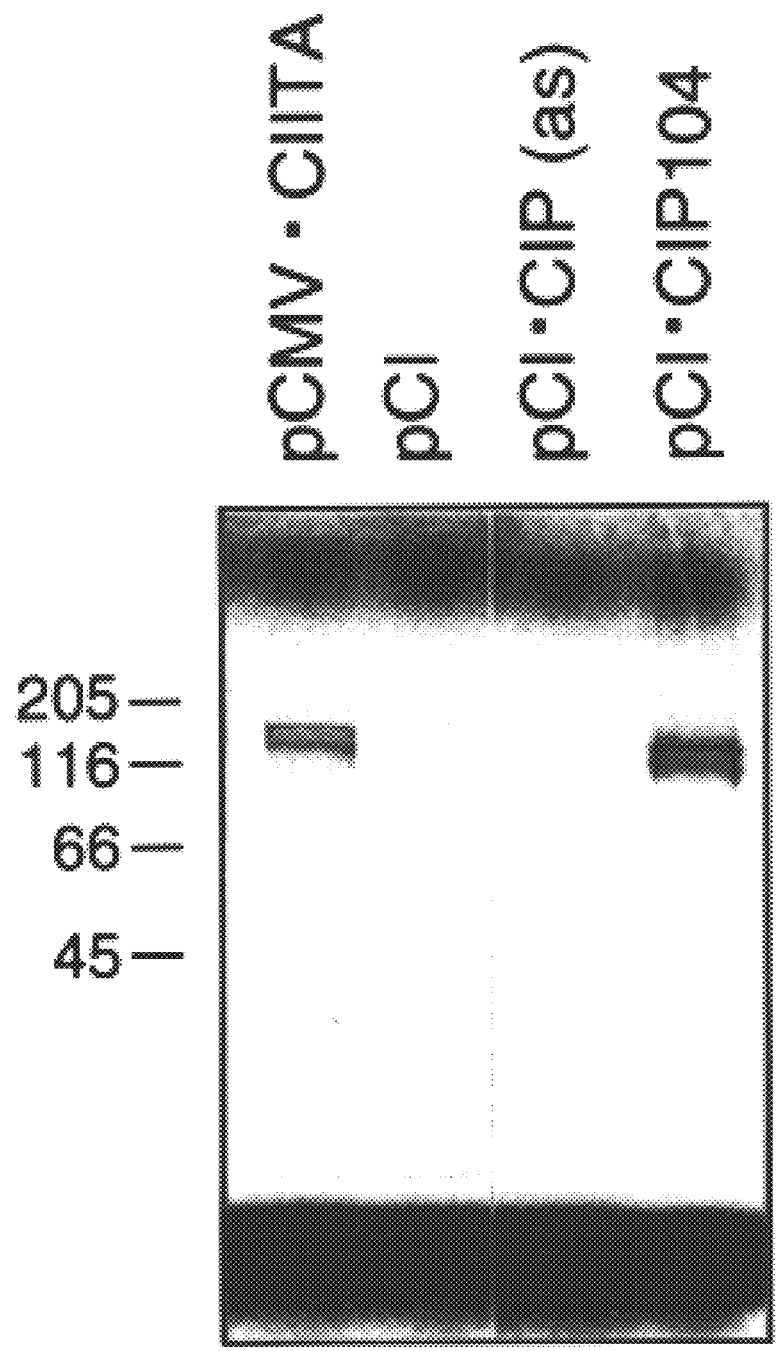
FIG. 2 is a photograph depicting expression of CIP104 protein, directed by the expression vector pCI.CIP104, in an in vitro reticulocyte lysate transcription/translation system. pCI.CIP104 (as) represents a control expression vector in which the CIP104-coding sequences are oriented in the antisense orientation, which fails to direct expression of a protein. pCI represents the parental control expression vector, which lacks CIP104 coding sequences. pCMV.CIITA represents a CIITA expression vector, which directs expression of CIITA protein.

To test for a functional role of CIP104 in regulating MHC gene transcription, the CIP104 cDNA was cloned into an expression vector and cotransfection experiments were performed. To ensure that CIP104 protein expression was directed by the CIP104 expression vector, in vitro reticulocyte lysate transcription/translation experiments were performed. As shown in FIG. 2, expression of the CIP104 cDNA, cloned into the pCI. CIP104 expression vector in the sense orientation, produced a protein of the expected molecular weight. In contrast, a control vector in which the CIP104 cDNA was cloned in the antisense orientation, pCI.CIP104 (as), did not result in protein production. The parental control vector, pCI, similarly did not direct protein expression. A CIITA expression vector, pCMV.CIITA, directed expression of a protein of the expected molecular weight.

Figure 3:
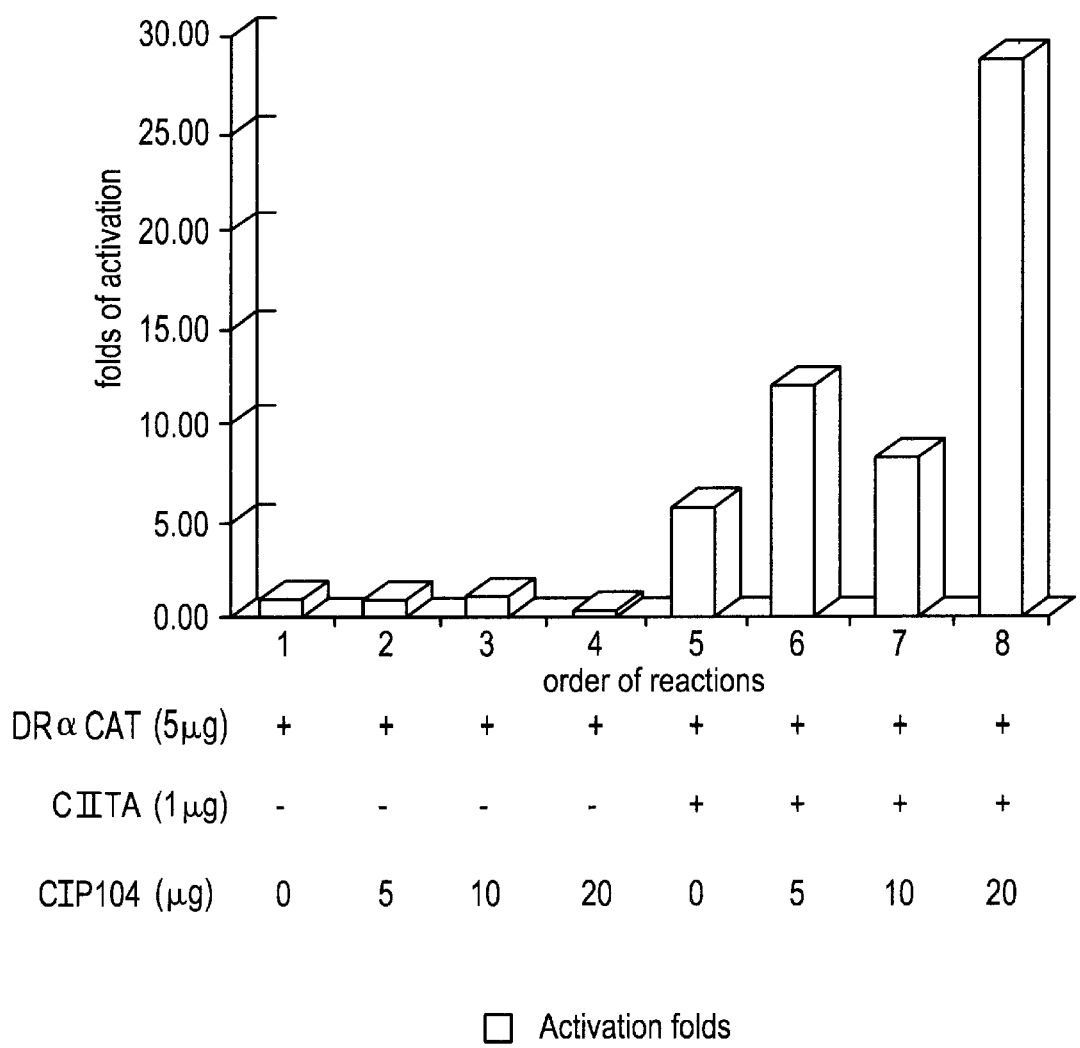
FIG. 3 is a bar graph depicting the effect of increasing amounts of CIP104 on transactivation of the human MHC class II DRα promoter, either in the absence (bars 1–4) or in presence (bars 5–8) of CIITA.

To test the transcriptional effect of CIP104, increasing amounts of the CIP104 expression vector (0, 5, 10 or 20 μg) were cotransfected into cells with either: (i) a DRα promoter-reporter gene construct (DRα-CAT) (5 μg) or (ii) both a DRα promoter-reporter gene construct (5 μg) and a CIITA expression vector (1 μg). The total amount of DNA transfected into each cell was brought to 26 μg using control vector DNA. The expression vector in which the CIP104 cDNA was cloned in the antisense orientation (pCI.CIP104 (as)) served as a control. The results of these studies are summarized in the graph of FIG. 3, which demonstrates that CIP104 alone (i.e., in the absence of CIITA) did not significantly stimulate expression of the DRα-CAT reporter gene (see bars 1–4 of FIG. 3). In contrast, when CIP104 was coexpressed with CIITA, transactivation of the DRα-CAT reporter gene was upregulated as compared to when CIITA was expressed alone (compare lane 5 of FIG. 3 with lanes 6–8). This effect of CIP104 was dose-dependent, with 20 μg of CIP104 stimulating CIITA-mediated DRα-CAT expression approximately 30-fold as compared to CIITA alone. No stimulation of CIITA-mediated DRα-CAT expression was observed with the pCI.CIP104 (as) antisense control vector. These experiments demonstrate that CIP104 can potentiate the transcriptional activation ability of CIITA for MHC class II promoters.

Figure 4:
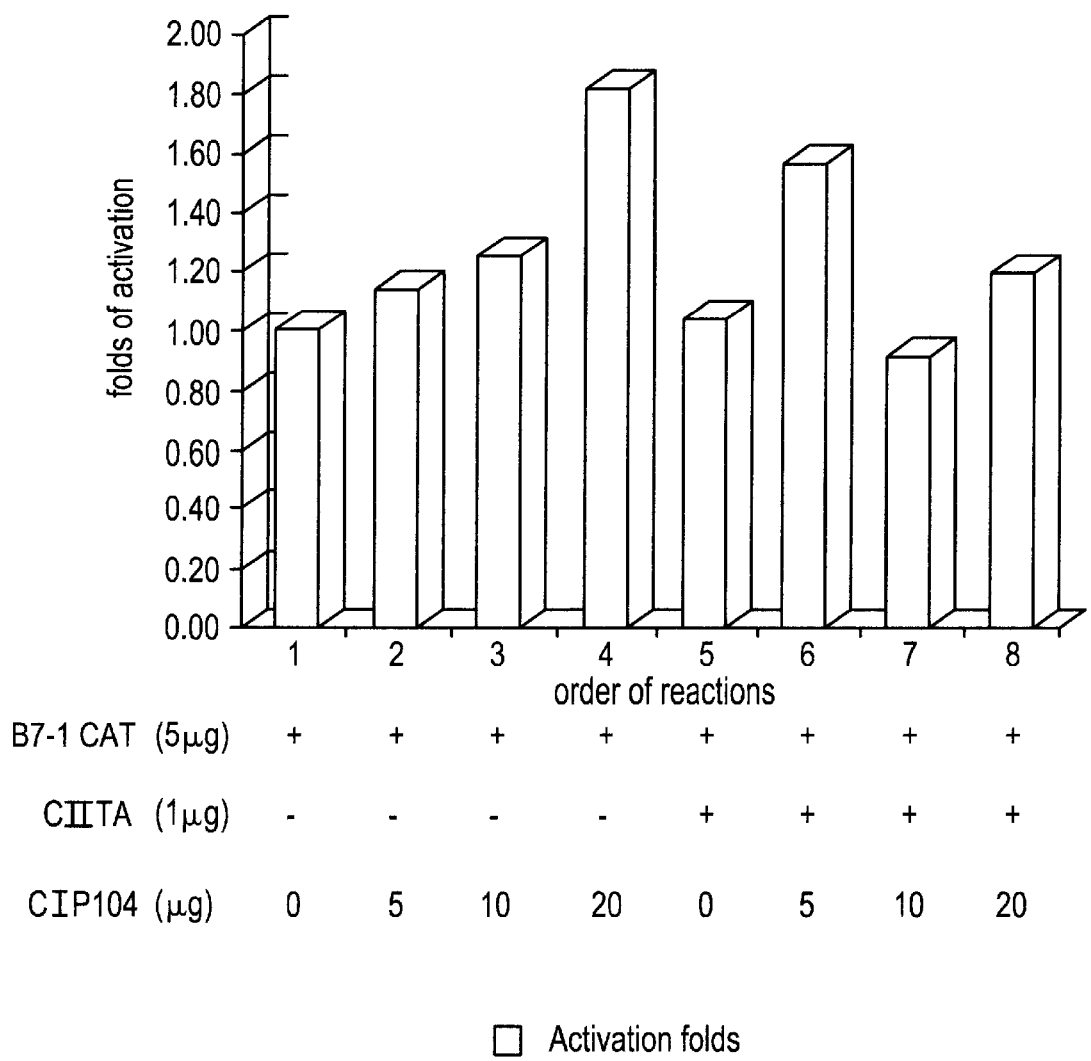
FIG. 4 is bar graph depicting the effect of increasing amounts of CIP104 on transactivation of the B7.1 promoter, either in the absence (bars 1–4) or in presence (bars 5-8) of CIITA.

A similar set of experiments were performed with a second reporter gene, pB7.1-CAT, to test the specificity of the effect. This reporter gene contains the B7.1 promoter linked to CAT. The results of these experiments are summarized in the graph of FIG. 4. In contrast to the results with the DRα-CAT reporter gene, no effect on transcription of the pB7.1-CAT reporter gene was observed when CIP104 and CIITA were coexpressed (see lanes 4–8). Moreover, CIP104 alone did not significantly stimulate B7.1-CAT expression. These results indicate that the synergistic effect of CIP104 and CIITA was not observed with a non-MHC class II promoter.

EQUIVALENTS

Those skilled in the art will recognize, or be able to ascertain using no more than routine experimentation, many equivalents to the specific embodiments of the invention described herein. Such equivalents are intended to be encompassed by the following claims.

---

We claim:

1. An isolated nucleic acid molecule comprising the coding region (positions 509–3343) of the nucleotide sequence of SEQ ID NO: 1.

2. The isolated nucleic acid molecule of claim 1, comprising the nucleotide sequence of SEQ ID NO: 1 (positions 1–4236).

3. An isolated nucleic acid molecule encoding the amino acid sequence of SEQ ID NO: 2 (positions 1–945).

4. A vector comprising the nucleic acid molecule of claim 3.

5. The vector of claim 4, which is an expression vector.

6. A host cell containing the vector of claim 5.

7. A method for producing a protein comprising the amino acid sequence of SEQ ID NO: 2, the method comprising culturing the host cell of claim 6 in a suitable medium until the protein encoded by the nucleic acid molecule is produced.

8. The method of claim 7, further comprising isolating the protein from the medium or the host cell.

* * * * *

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 4236 base pairs
      (B) TYPE: nucleic acid
      (C) STRANDEDNESS: single
      (D) TOPOLOGY: linear (ii) MOLECULE TYPE: cDNA (ix) FEATURE:

(A) NAME/KEY: CDS
(B) LOCATION: 509..3343

(xi) SEQUENCE DESCRIPTION: SEQ ID NO:1:

```
GTCGACTACG TGTGTTTGTT GCGAGGTGTG AGACAACATT TTGTTTGATC A TTTATTTTG      60

GGCTGTTGTA ATGGTGTGAG TGTGCGTTTT TTATTTTTTT GGAAGTGGGG T TTTAGACTA     120

GACTGTAGTG AGCAATCTTT GCCTGCCGGC TTTCAAGGGA TTTTCCTGCT T CAGTCTCCC     180

AGCCCAGCAC AGAACCCCCA GGACCCACCT CTTGTACCCC TGACTCTTGC C CTGCCTCCA     240

GCCCCTCCTT CCTCCTGCCA CCAAAATACC TCAGGAAGCT TCAGGCGCGC G GAGAGCCCT     300

GGCCCAGGGT CTCCTTCCCA AAGACCCCGA GGTGGGGCCG GGGCCACCCC C AGGCCCCCT     360

GAGTAAAGCC CCCCAGCCTG TGCCGCCCGG GGTTGGGGAG CTGCCTGCCC G AGGCCCTCG     420

ACTCTTTGAT TTTCCCCCCA CTCCGCTGGA GGACCAGTTT GAGGAGCCAG C CGAATTCAA     480

GATCCTACCT GATGGGCTGG CCAACATC ATG AAG ATG CTG GAC  GAA TCC ATT        532
                                Met Lys Met Leu Asp Glu Ser Ile
                                 1               5
```

| | | | | | | | | |
|---|---|---|---|---|---|---|---|---|
| CGC AAG GAA GAG GAA CAG CAA CAA CAC GAA G CA GGC GTG GCC CCC CAA | | | | | | | | 580 |
| Arg Lys Glu Glu Glu Gln Gln Gln His Glu A la Gly Val Ala Pro Gln | | | | | | | | |
| 10 | | | 15 | | | 20 | | |

```
CCC CCG CTG AAG GAG CCC TTT GCA TCT CTG C AG TCT CCT TTC CCC ACC        628
Pro Pro Leu Lys Glu Pro Phe Ala Ser Leu G ln Ser Pro Phe Pro Thr
 25              30                35                  40

GAC ACA GCC CCC ACC ACT ACT GCT CCT GCT G TC GCC GTC ACC ACC ACC        676
Asp Thr Ala Pro Thr Thr Thr Ala Pro Ala V al Ala Val Thr Thr Thr
                 45                50                  55

ACC ACC ACC ACC ACC ACC ACG GCC ACC C AG GAA GAG GAG AAG AAG           724
Thr Thr Thr Thr Thr Thr Thr Ala Thr G ln Glu Glu Glu Lys Lys
             60                65               70

CCA CCA CCA GCC CTA CCA CCA CCA CCG CCT C TA GCC AAG TTC CCT CCA        772
Pro Pro Pro Ala Leu Pro Pro Pro Pro Pro L eu Ala Lys Phe Pro Pro
 75              80                          85

CCC TCT CAG CCA CAG CCA CCA CCA CCC CCA C CC CCC AGC CCG GCC AGC        820
Pro Ser Gln Pro Gln Pro Pro Pro Pro Pro P ro Pro Ser Pro Ala Ser
 90              95                      100

CTG CTC AAA TCC TTG GCC TCC GTG CTG GAG G GA CAA AAG TAC TGT TAT        868
Leu Leu Lys Ser Leu Ala Ser Val Leu Glu G ly Gln Lys Tyr Cys Tyr
105             110               115                 120

CGG GGG ACT GGA GCA GCT GTT TCC ACC CGG C CT GGG CCC TTG CCC ACC        916
Arg Gly Thr Gly Ala Ala Val Ser Thr Arg P ro Gly Pro Leu Pro Thr
                125               130                 135

ACT CAG TAT TCC CCT GGC CCC CCA TCA GGT G CT ACC GCC CTG CCG CCC        964
Thr Gln Tyr Ser Pro Gly Pro Pro Ser Gly A la Thr Ala Leu Pro Pro
            140               145                 150

ACC TCA GCG GCC CCT AGC GCC CAG GGC TCC C CA CAG CCC TCT GCT TCC       1012
Thr Ser Ala Ala Pro Ser Ala Gln Gly Ser P ro Gln Pro Ser Ala Ser
            155               160                 165

TCG TCA TCT CAG TTC TCT ACC TCA GGC GGG C CC TGG GCC CGG GAG CGC       1060
Ser Ser Ser Gln Phe Ser Thr Ser Gly Gly P ro Trp Ala Arg Glu Arg
            170               175                 180

AGG GCG GGC GAA GAG CCA GTC CCG GGC CCC A TG ACC CCC ACC CAA CCG       1108
Arg Ala Gly Glu Glu Pro Val Pro Gly Pro M et Thr Pro Thr Gln Pro
185             190               195                 200

CCC CCA CCC CTA TCT CTG CCC CCT GCT CGC T CT GAG TCT GAG GTG CTA       1156
Pro Pro Pro Leu Ser Leu Pro Pro Ala Arg S er Glu Ser Glu Val Leu
                205               210                 215

GAA GAG ATC AGC CGG GCT TGC GAG ACC CTT G TG GAG CGG GTG GGC CGG       1204
Glu Glu Ile Ser Arg Ala Cys Glu Thr Leu V al Glu Arg Val Gly Arg
```

-continued

```
              220                 225                 230
AGT GCC ACT GAC CCA GCC GAC CCA GTG GAC A CA GCA GAG CCA GCG GAC          1252
Ser Ala Thr Asp Pro Ala Asp Pro Val Asp T hr Ala Glu Pro Ala Asp
            235                 240                 245

AGT GGG ACT GAG CGA CTG CTG CCC CCC GCA C AG GCC AAG GAG GAG GCT          1300
Ser Gly Thr Glu Arg Leu Leu Pro Pro Ala G ln Ala Lys Glu Glu Ala
        250                 255                 260

GGC GGG GTG GCG GCA GTG TCA GGC AGC TGT A AG CGG CGA CAG AAG GAG          1348
Gly Gly Val Ala Ala Val Ser Gly Ser Cys L ys Arg Arg Gln Lys Glu
265                 270                 275                 280

CAT CAG AAG GAG CAT CGG CGG CAC AGG CGG G CC TGT AAG GAC AGT GTG          1396
His Gln Lys Glu His Arg Arg His Arg Arg A la Cys Lys Asp Ser Val
                285                 290                 295

GGT CGT CGG CCC CGT GAG GGC AGG GCA AAG G CC AAG GCC AAG GTC CCC          1444
Gly Arg Arg Pro Arg Glu Gly Arg Ala Lys A la Lys Ala Lys Val Pro
            300                 305                 310

AAA GAA AAG AGC CGC CGG GTG CTG GGG AAC C TG GAC CTG CAG AGC GAG          1492
Lys Glu Lys Ser Arg Arg Val Leu Gly Asn L eu Asp Leu Gln Ser Glu
        315                 320                 325

GAG ATC CAG GGT CGT GAG AAG TCC CGG CCC G AT CTT GGC GGG GCC TCC          1540
Glu Ile Gln Gly Arg Glu Lys Ser Arg Pro A sp Leu Gly Gly Ala Ser
330                 335                 340

AAG GCC AAG CCA CCC ACA GCT CCA GCC CCT C CA TCA GCT CCT GCA CCT          1588
Lys Ala Lys Pro Pro Thr Ala Pro Ala Pro P ro Ser Ala Pro Ala Pro
345                 350                 355                 360

TCT GCC CAG CCC ACA CCC CCG TCA GCC TCT G TC CCT GGA AAG AAG GCT          1636
Ser Ala Gln Pro Thr Pro Pro Ser Ala Ser V al Pro Gly Lys Lys Ala
            365                 370                 375

CGG GAG GAA GCC CCA GGG CCA CCG GGT GTC A GC CGG GCC GAC ATG CTG          1684
Arg Glu Glu Ala Pro Gly Pro Pro Gly Val S er Arg Ala Asp Met Leu
        380                 385                 390

AAG CTG CGC TCA CTT AGT GAG GGG CCC CCC A AG GAG CTG AAG ATC CGG          1732
Lys Leu Arg Ser Leu Ser Glu Gly Pro Pro L ys Glu Leu Lys Ile Arg
    395                 400                 405

CTC ATC AAG GTA GAG AGT GGT GAC AAG GAG A CC TTT ATC GCC TCT GAG          1780
Leu Ile Lys Val Glu Ser Gly Asp Lys Glu T hr Phe Ile Ala Ser Glu
    410                 415                 420

GTG GAA GAG CGG CGG CTG CGC ATG GCA GAC C TC ACC ATC AGC CAC TGT          1828
Val Glu Glu Arg Arg Leu Arg Met Ala Asp L eu Thr Ile Ser His Cys
425                 430                 435                 440

GCT GCT GAC GTC GTG CGC GCC AGC AGG AAT G CC AAG GTG AAA GGG AAG          1876
Ala Ala Asp Val Val Arg Ala Ser Arg Asn A la Lys Val Lys Gly Lys
                445                 450                 455

TTT CGA GAG TCC TAC CTT TCC CCT GCC CAG T CT GTG AAA CCG AAG ATC          1924
Phe Arg Glu Ser Tyr Leu Ser Pro Ala Gln S er Val Lys Pro Lys Ile
            460                 465                 470

AAC ACT GAG GAG AAG CTG CCC CGG GAA AAA C TC AAC CCC CCT ACA CCC          1972
Asn Thr Glu Glu Lys Leu Pro Arg Glu Lys L eu Asn Pro Pro Thr Pro
        475                 480                 485

AGC ATC TAT CTG GAG AGC AAA CGG GAT GCC T TC TCA CCT GTC CTG CTG          2020
Ser Ile Tyr Leu Glu Ser Lys Arg Asp Ala P he Ser Pro Val Leu Leu
            490                 495                 500

CAG TTC TGT ACA GAC CCT CGA AAT CCC ATC A CA GTG ATC CGG GGC CTG          2068
Gln Phe Cys Thr Asp Pro Arg Asn Pro Ile T hr Val Ile Arg Gly Leu
505                 510                 515                 520

GCG GGC TCC CTG CGG CTC AAC TTG GGC CTC T TC TCC ACC AAG ACC CTG          2116
Ala Gly Ser Leu Arg Leu Asn Leu Gly Leu P he Ser Thr Lys Thr Leu
                525                 530                 535

GTG GAA GCG AGT GGC GAA CAC ACC GTG GAA G TT CGC ACC CAG GTG CAG          2164
```

-continued

```
Val Glu Ala Ser Gly Glu His Thr Val Glu Val Arg Thr Gln Val Gln
            540                 545                 550

CAG CCC TCA GAT GAG AAC TGG GAT CTG ACA GGC ACT CGG CAG ATC TGG    2212
Gln Pro Ser Asp Glu Asn Trp Asp Leu Thr Gly Thr Arg Gln Ile Trp
        555                 560                 565

CCT TGT GAG AGC TCC CGT TCC CAC ACC ACC ATT GCC AAG TAC GCA CAG    2260
Pro Cys Glu Ser Ser Arg Ser His Thr Thr Ile Ala Lys Tyr Ala Gln
570                 575                 580

TAC CAG GCC TCA TCC TTC CAG GAG TCT CTG CAG GAG GAG AAG GAG AGT    2308
Tyr Gln Ala Ser Ser Phe Gln Glu Ser Leu Gln Glu Glu Lys Glu Ser
585                 590                 595                 600

GAG GAT GAG GAG TCA GAG GAG CCA GAC AGC ACC ACT GGA ACC CCT CCT    2356
Glu Asp Glu Glu Ser Glu Glu Pro Asp Ser Thr Thr Gly Thr Pro Pro
                605                 610                 615

AGC AGC GCA CCA GAC CCG AAG AAC CAT CAC ATC ATC AAG TTT GGC ACC    2404
Ser Ser Ala Pro Asp Pro Lys Asn His His Ile Ile Lys Phe Gly Thr
            620                 625                 630

AAC ATC GAC TTG TCT GAT GCT AAG CGG TGG AAG CCC CAG CTG CAG GAG    2452
Asn Ile Asp Leu Ser Asp Ala Lys Arg Trp Lys Pro Gln Leu Gln Glu
            635                 640                 645

CTG CTG AAG CTG CCC GCC TTC ATG CGG GTA ACA TCC ACG GGC AAC ATG    2500
Leu Leu Lys Leu Pro Ala Phe Met Arg Val Thr Ser Thr Gly Asn Met
    650                 655                 660

CTG AGC CAC GTG GGC CAC ACC ATC CTG GGC ATG AAC ACG GTG CAG CTG    2548
Leu Ser His Val Gly His Thr Ile Leu Gly Met Asn Thr Val Gln Leu
665                 670                 675                 680

TAC ATG AAG GTG CCC GGC AGC CGA ACG CCA GGC CAC CAG GAG AAT AAC    2596
Tyr Met Lys Val Pro Gly Ser Arg Thr Pro Gly His Gln Glu Asn Asn
                685                 690                 695

AAC TTC TGG TCC GTC AAC ATC AAC ATT GGC CCA GGC GAC TGC GAG TGG    2644
Asn Phe Trp Ser Val Asn Ile Asn Ile Gly Pro Gly Asp Cys Glu Trp
            700                 705                 710

TTC GCG GTG CAC GAG CAC TAC TGG GAG ACC ATC AGG GCT TTC TGT GAT    2692
Phe Ala Val His Glu His Tyr Trp Glu Thr Ile Arg Ala Phe Cys Asp
            715                 720                 725

CGG CAC GGC GTG GAC TAC TTG ACG GGT TCC TGG TGG CCA ATC CTG GAT    2740
Arg His Gly Val Asp Tyr Leu Thr Gly Ser Trp Trp Pro Ile Leu Asp
        730                 735                 740

GAT CTC TAT GCA TCC AAT ATT CCT GTG TAC CGC TTC GTG CAG CGA CCC    2788
Asp Leu Tyr Ala Ser Asn Ile Pro Val Tyr Arg Phe Val Gln Arg Pro
745                 750                 755                 760

GGA GAC CTC GTG TGG ATT AAT GCG GGG ACT GTG CAC TGG GTG CAG GCC    2836
Gly Asp Leu Val Trp Ile Asn Ala Gly Thr Val His Trp Val Gln Ala
                765                 770                 775

ACC GGC TGG TGC AAC AAC ATT GCC TGG AAC GTG GGG CCC CTC ACC GCC    2884
Thr Gly Trp Cys Asn Asn Ile Ala Trp Asn Val Gly Pro Leu Thr Ala
            780                 785                 790

TAT CAG TAC CAG CTG GCC CTG GAA CGA TAC GAG TGG AAT GAG GTG AAG    2932
Tyr Gln Tyr Gln Leu Ala Leu Glu Arg Tyr Glu Trp Asn Glu Val Lys
            795                 800                 805

AAC GTC AAA TCC ATC GTG CCC ATG ATT CAC GTG TCA TGG AAC GTG GCT    2980
Asn Val Lys Ser Ile Val Pro Met Ile His Val Ser Trp Asn Val Ala
    810                 815                 820

CGC ACG GTC AAA ATC AGC GAC CCC GAC TTG TTC AAG ATG ATC AAG TTC    3028
Arg Thr Val Lys Ile Ser Asp Pro Asp Leu Phe Lys Met Ile Lys Phe
825                 830                 835                 840

TGC CTG CTG CAG TCC ATG AAG CAC TGC CAG GTG CAA CGC GAG AGC CTG    3076
Cys Leu Leu Gln Ser Met Lys His Cys Gln Val Gln Arg Glu Ser Leu
                845                 850                 855
```

```
GTG CGG GCA GGG AAG AAA ATC GCT TAC CAG G GC CGT GTC AAG GAC GAG    3124
Val Arg Ala Gly Lys Lys Ile Ala Tyr Gln G ly Arg Val Lys Asp Glu
            860             865             870

CCA GCC TAC TAC TGC AAC GAC TGC GAT GTG G AG GTG TTT AAC ATC CTG    3172
Pro Ala Tyr Tyr Cys Asn Asp Cys Asp Val G lu Val Phe Asn Ile Leu
            875             880             885

TTC GTG ACA AGT GAG AAT GGC AGC CGC AAC A CG TAC CTG GTA CAC TGC    3220
Phe Val Thr Ser Glu Asn Gly Ser Arg Asn T hr Tyr Leu Val His Cys
            890             895             900

GAG GGC TGT GCC CGG CGC CGC AGC GCA GGC C TG CAG GGC GTG GTG GTG    3268
Glu Gly Cys Ala Arg Arg Arg Ser Ala Gly L eu Gln Gly Val Val Val
905             910             915                         920

CTG GAG CAG TAC CGC ACT GAG GAG CTG GCT C AG GCC TAC GAC GCC TTC    3316
Leu Glu Gln Tyr Arg Thr Glu Glu Leu Ala G ln Ala Tyr Asp Ala Phe
                925             930             935

ACG CTG GCC CCA GCC AGC ACG TCG CGA TGAGGCCG GA CGCCCCGCCC          3363
Thr Leu Ala Pro Ala Ser Thr Ser Arg
            940             945

GCCTGCCTGC CCGCGCAACG CGCCGCGGGG CCACCAGCAC ATGCCTGGGC T GGGCCTAGG  3423

TCCCGCCTGT GGCCGAGAAG GGGGTCGGGC CCAGCCCTTC CACCCCATTG G CAGCTCCCC  3483

TCACTTAATT TATTAAGAAA AACTTTTTTT TTTTTTAGCA AATATGAGGA A AAAAGGAAA  3543

AAAAATGGGA GACGGGGGAG GGGGCTGGCA GCCCCTCGCC CACCAGCGCC T CCCCTCACC  3603

GACTTTGGCC TTTTTAGCAA CAGACACAAG GACCAGGCTC CGGCGGCGGC G GGGTCACA   3663

TACGGGTTCC CTCACCCTGC CAGCCGCCCG CCCGCCCGGC GCAGATGCAC G CGGCTCGTG  3723

TATGTACATA GACGTTACGG CAGCCGAGGT TTTTAATGAG ATTCTTTCTA T GGGCTTTAC  3783

CCCTCCCCCG GAACCTCCTT TTTTACTTCC AATGCTAGCT GTGACCCCTG T ACATGTCTC  3843

TTTATTCACT TGGTTATGAT TTGTATTTTT TGTTCTTTTC TTGTTTTTTT G TTTTTAATT  3903

TATAACAGTC CCACTCACCT CTATTTATTC ATTTTTGGGA AAACCCGACC T CCCACACCC  3963

CCAAGCCATC CTGCCCGCCC CTCCAGGGAC CGCCCGTCGC CGGGCTCTCC C CGCGCCCCA  4023

GTGTGTGTCC GGGCCCGGCC CGACCGTCTC CACCCGTCCG CCCGCGGCTC C AGCCGGGTT  4083

CTCATGGTGC TCAAACCCGC TCCCCTCCCC TACGTCCTGC ACTTTCTCGG A CCAGTCCCC  4143

CCACTCCCGA CCCGACCCCA GCCCCACCTG AGGGTGAGCA ACTCCTGTAC T GTAGGGGAA  4203

GAAGTGGGAA CTGAAATGGT ATTTTATGTA GTC                                4236

(2) INFORMATION FOR SEQ ID NO:2:

(i) SEQUENCE CHARACTERISTICS:
        (A) LENGTH: 945 amino acids
        (B) TYPE: amino acid
        (D) TOPOLOGY: linear (ii) MOLECULE TYPE: protein (xi) SEQUENCE DESCRIPTION: SEQ ID NO:2:

Met Lys Met Leu Asp Glu Ser Ile Arg Lys G lu Glu Glu Gln Gln Gln
1               5               10              15

His Glu Ala Gly Val Ala Pro Gln Pro Pro L eu Lys Glu Pro Phe Ala
            20              25              30

Ser Leu Gln Ser Pro Phe Pro Thr Asp Thr A la Pro Thr Thr Thr Ala
        35              40              45

Pro Ala Val Ala Val Thr Thr Thr Thr T hr Thr Thr Thr Thr
        50              55              60

Ala Thr Gln Glu Glu Glu Lys Lys Pro Pro P ro Ala Leu Pro Pro Pro
```

```
           65                  70                  75                  80
  Pro Pro Leu Ala Lys Phe Pro Pro Ser Gln Pro Gln Pro Pro Pro
                   85                  90                  95

Pro Pro Pro Ser Pro Ala Ser Leu Leu Lys Ser Leu Ala Ser Val
              100                 105                 110

Leu Glu Gly Gln Lys Tyr Cys Tyr Arg Gly Thr Gly Ala Ala Val Ser
              115                 120                 125

Thr Arg Pro Gly Pro Leu Pro Thr Thr Gln Tyr Ser Pro Gly Pro Pro
              130                 135                 140

Ser Gly Ala Thr Ala Leu Pro Pro Thr Ser Ala Ala Pro Ser Ala Gln
  145                 150                 155                 160

Gly Ser Pro Gln Pro Ser Ala Ser Ser Ser Gln Phe Ser Thr Ser
                  165                 170                 175

Gly Gly Pro Trp Ala Arg Glu Arg Arg Ala Gly Glu Glu Pro Val Pro
              180                 185                 190

Gly Pro Met Thr Pro Thr Gln Pro Pro Pro Leu Ser Leu Pro Pro
              195                 200                 205

Ala Arg Ser Glu Ser Glu Val Leu Glu Glu Ile Ser Arg Ala Cys Glu
              210                 215                 220

Thr Leu Val Glu Arg Val Gly Arg Ser Ala Thr Asp Pro Ala Asp Pro
  225                 230                 235                 240

Val Asp Thr Ala Glu Pro Ala Asp Ser Gly Thr Glu Arg Leu Leu Pro
              245                 250                 255

Pro Ala Gln Ala Lys Glu Glu Ala Gly Gly Val Ala Ala Val Ser Gly
              260                 265                 270

Ser Cys Lys Arg Arg Gln Lys Glu His Gln Lys Glu His Arg Arg His
              275                 280                 285

Arg Arg Ala Cys Lys Asp Ser Val Gly Arg Arg Pro Arg Glu Gly Arg
  290                 295                 300

Ala Lys Ala Lys Ala Lys Val Pro Lys Glu Lys Ser Arg Arg Val Leu
  305                 310                 315                 320

Gly Asn Leu Asp Leu Gln Ser Glu Glu Ile Gln Gly Arg Glu Lys Ser
                  325                 330                 335

Arg Pro Asp Leu Gly Gly Ala Ser Lys Ala Lys Pro Pro Thr Ala Pro
                  340                 345                 350

Ala Pro Pro Ser Ala Pro Ala Pro Ser Ala Gln Pro Thr Pro Pro Ser
              355                 360                 365

Ala Ser Val Pro Gly Lys Lys Ala Arg Glu Glu Ala Pro Gly Pro Pro
  370                 375                 380

Gly Val Ser Arg Ala Asp Met Leu Lys Leu Arg Ser Leu Ser Glu Gly
  385                 390                 395                 400

Pro Pro Lys Glu Leu Lys Ile Arg Leu Ile Lys Val Glu Ser Gly Asp
                  405                 410                 415

Lys Glu Thr Phe Ile Ala Ser Glu Val Glu Glu Arg Arg Leu Arg Met
              420                 425                 430

Ala Asp Leu Thr Ile Ser His Cys Ala Ala Asp Val Val Arg Ala Ser
              435                 440                 445

Arg Asn Ala Lys Val Lys Gly Lys Phe Arg Glu Ser Tyr Leu Ser Pro
  450                 455                 460

Ala Gln Ser Val Lys Pro Lys Ile Asn Thr Glu Glu Lys Leu Pro Arg
  465                 470                 475                 480

Glu Lys Leu Asn Pro Pro Thr Pro Ser Ile Tyr Leu Glu Ser Lys Arg
                  485                 490                 495
```

-continued

```
Asp Ala Phe Ser Pro Val Leu Leu Gln Phe Cys Thr Asp Pro Arg Asn
            500                 505                 510
Pro Ile Thr Val Ile Arg Gly Leu Ala Gly Ser Leu Arg Leu Asn Leu
        515                 520                 525
Gly Leu Phe Ser Thr Lys Thr Leu Val Glu Ala Ser Gly Glu His Thr
    530                 535                 540
Val Glu Val Arg Thr Gln Val Gln Gln Pro Ser Asp Glu Asn Trp Asp
545                 550                 555                 560
Leu Thr Gly Thr Arg Gln Ile Trp Pro Cys Glu Ser Ser Arg Ser His
                565                 570                 575
Thr Thr Ile Ala Lys Tyr Ala Gln Tyr Gln Ala Ser Ser Phe Gln Glu
            580                 585                 590
Ser Leu Gln Glu Glu Lys Glu Ser Glu Asp Glu Glu Ser Glu Glu Pro
        595                 600                 605
Asp Ser Thr Thr Gly Thr Pro Pro Ser Ser Ala Pro Asp Pro Lys Asn
    610                 615                 620
His His Ile Ile Lys Phe Gly Thr Asn Ile Asp Leu Ser Asp Ala Lys
625                 630                 635                 640
Arg Trp Lys Pro Gln Leu Gln Glu Leu Leu Lys Leu Pro Ala Phe Met
                645                 650                 655
Arg Val Thr Ser Thr Gly Asn Met Leu Ser His Val Gly His Thr Ile
            660                 665                 670
Leu Gly Met Asn Thr Val Gln Leu Tyr Met Lys Val Pro Gly Ser Arg
        675                 680                 685
Thr Pro Gly His Gln Glu Asn Asn Asn Phe Trp Ser Val Asn Ile Asn
    690                 695                 700
Ile Gly Pro Gly Asp Cys Glu Trp Phe Ala Val His Glu His Tyr Trp
705                 710                 715                 720
Glu Thr Ile Arg Ala Phe Cys Asp Arg His Gly Val Asp Tyr Leu Thr
                725                 730                 735
Gly Ser Trp Trp Pro Ile Leu Asp Asp Leu Tyr Ala Ser Asn Ile Pro
            740                 745                 750
Val Tyr Arg Phe Val Gln Arg Pro Gly Asp Leu Val Trp Ile Asn Ala
        755                 760                 765
Gly Thr Val His Trp Val Gln Ala Thr Gly Trp Cys Asn Asn Ile Ala
    770                 775                 780
Trp Asn Val Gly Pro Leu Thr Ala Tyr Gln Tyr Gln Leu Ala Leu Glu
785                 790                 795                 800
Arg Tyr Glu Trp Asn Glu Val Lys Asn Val Lys Ser Ile Val Pro Met
                805                 810                 815
Ile His Val Ser Trp Asn Val Ala Arg Thr Val Lys Ile Ser Asp Pro
            820                 825                 830
Asp Leu Phe Lys Met Ile Lys Phe Cys Leu Leu Gln Ser Met Lys His
        835                 840                 845
Cys Gln Val Gln Arg Glu Ser Leu Val Arg Ala Gly Lys Lys Ile Ala
    850                 855                 860
Tyr Gln Gly Arg Val Lys Asp Glu Pro Ala Tyr Tyr Cys Asn Asp Cys
865                 870                 875                 880
Asp Val Glu Val Phe Asn Ile Leu Phe Val Thr Ser Glu Asn Gly Ser
                885                 890                 895
Arg Asn Thr Tyr Leu Val His Cys Glu Gly Cys Ala Arg Arg Arg Ser
            900                 905                 910
```

```
Ala Gly Leu Gln Gly Val Val Val Leu Glu G ln Tyr Arg Thr Glu Glu
        915             920             925

Leu Ala Gln Ala Tyr Asp Ala Phe Thr Leu A la Pro Ala Ser Thr Ser
        930             935             940

Arg
945
```